(12) United States Patent
Demarest et al.

(10) Patent No.: US 9,901,744 B2
(45) Date of Patent: Feb. 27, 2018

(54) ORAL TREATMENT DEVICE

(71) Applicant: COLGATE-PALMOLIVE COMPANY, New York, NY (US)

(72) Inventors: Scott Demarest, Basking Ridge, NJ (US); Francis Tatu, Manlius, NY (US); Mark Bartlett, North East, PA (US); Evaristo Delgado, Piscataway, NJ (US); Kathryn Neal, Piscataway, NJ (US); Patrik Johansson, Hoboken, NJ (US); Mark Lowenthal, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/979,157

(22) Filed: Dec. 22, 2015

(65) Prior Publication Data

US 2017/0173356 A1 Jun. 22, 2017

(51) Int. Cl.
*A61N 5/06* (2006.01)
*A61C 5/14* (2006.01)

(52) U.S. Cl.
CPC .............. *A61N 5/0603* (2013.01); *A61C 5/14* (2013.01); *A61N 5/0613* (2013.01);
(Continued)

(58) Field of Classification Search
CPC ......... A61C 5/14; A61C 19/06; A61C 19/066; A61N 5/0613; A61N 2005/0644; A61N 2005/0663; A61N 2005/0606
(Continued)

(56) References Cited

U.S. PATENT DOCUMENTS 5,316,473 A * 5/1994 Hare .................... A61C 19/004
433/215
6,616,447 B1 * 9/2003 Rizoiu ................. A61C 19/063
433/216
(Continued)

FOREIGN PATENT DOCUMENTS

EP         1054642         5/2008
KR    1015251238 B1 *  6/2015 ............. A61C 19/06
(Continued)

OTHER PUBLICATIONS

Barolet, "Light-Emitting Diodes (LEDs) in Dermatology," Semin Cutan Med Surg. 2008; 27: 227-238.
(Continued)

*Primary Examiner* — Nicholas Lucchesi
*Assistant Examiner* — Shannel Wright

(57) ABSTRACT

An oral treatment device that emits light onto surfaces of a user's teeth. In one aspect, the oral treatment device includes an intraoral mouthpiece. The mouthpiece may comprise a lamp support structure comprising a lamp support surface; first and second lamps, each of the first and second lamps comprising a plurality of light emitters that generate light which is emitted from a rear surface of the lamp; each of the first and second lamps mounted to the lamp support surface, thereby forming a lamp assembly, each of the first and second lamps operably coupled to a control circuit having a power source; and a lamp retaining component coupled to the lamp support structure, a lower portion of the first lamp and an upper portion of the second lamp retained between the lamp retaining component and the lamp support surface of the lamp support structure.

16 Claims, 25 Drawing Sheets

(52) U.S. Cl.
CPC .............. *A61N 2005/0606* (2013.01); *A61N 2005/0644* (2013.01); *A61N 2005/0663* (2013.01)

(58) Field of Classification Search
USPC .................................. 433/29, 216, 215, 125
See application file for complete search history.

(56) References Cited

U.S. PATENT DOCUMENTS

| | | | |
|---|---|---|---|
| 6,893,259 B1* | 5/2005 | Reizenson | A61C 17/0211 433/29 |
| 7,331,784 B2* | 2/2008 | Suzuki | A61C 19/063 433/29 |
| 7,645,137 B2 | 1/2010 | Wasyluch | |
| 7,802,988 B2 | 9/2010 | Yarborough | |
| 8,172,570 B2* | 5/2012 | Baughman | A61C 5/00 433/216 |
| 8,215,954 B2* | 7/2012 | Levine | A61C 19/063 433/215 |
| 8,591,227 B2* | 11/2013 | Levine | A61C 19/063 433/215 |
| 8,602,774 B2 | 12/2013 | Wasyluch | |
| 2005/0048444 A1* | 3/2005 | Creamer | A61C 19/066 433/215 |
| 2006/0141422 A1* | 6/2006 | Philp, Jr. | A61C 19/063 433/215 |
| 2008/0032253 A1 | 2/2008 | Montgomery et al. | |
| 2008/0063999 A1* | 3/2008 | Osborn | A61C 19/063 433/29 |
| 2008/0233541 A1* | 9/2008 | De Vreese | A61C 19/066 433/216 |
| 2009/0017422 A1* | 1/2009 | Creamer | A61C 19/066 433/215 |
| 2011/0076636 A1* | 3/2011 | Wolff | A61C 19/063 433/27 |
| 2011/0104631 A1* | 5/2011 | Levine | A61C 19/063 433/29 |
| 2012/0214122 A1* | 8/2012 | Dwyer | A61C 19/066 433/29 |
| 2013/0045457 A1* | 2/2013 | Chetiar | A61N 5/0601 433/29 |
| 2013/0175515 A1* | 7/2013 | Ray | F21K 9/23 257/40 |
| 2013/0280671 A1* | 10/2013 | Brawn | A61N 5/0603 433/24 |
| 2014/0227657 A1* | 8/2014 | Sanders | A61C 19/066 433/32 |
| 2014/0272770 A1* | 9/2014 | Hurley | A61C 19/063 433/29 |
| 2014/0355251 A1* | 12/2014 | Kahrs | F21V 33/0052 362/97.1 |
| 2015/0004556 A1* | 1/2015 | Jin | A61C 5/125 433/29 |
| 2015/0044628 A1* | 2/2015 | Flyash | A61C 19/066 433/27 |
| 2015/0132709 A1* | 5/2015 | Park | A61N 5/0603 433/29 |
| 2016/0271415 A1* | 9/2016 | Min | A61C 19/066 |

FOREIGN PATENT DOCUMENTS

| | | |
|---|---|---|
| WO | WO2006020128 | 2/2006 |
| WO | WO2010098761 | 9/2010 |
| WO | WO2011159522 | 12/2011 |
| WO | WO2011163220 | 12/2011 |
| WO | WO2013093743 | 6/2013 |

OTHER PUBLICATIONS

Belikov et al., "Study of the dynamics of the absorption spectra of human tooth enamel and dentine under heating and ablation by submillisecond pulse radiation of an erbium laser with a generation wavelength of 2.79um," Optics and Spectroscopy, 2010, 109(2):211-216.

Brodbelt et al., "Translucency of Human dental enamel," J Dent. Res. 1981, 60: 1749-1753.

De Moor et al., "The Use of the KTP Laser, an Added Value for Tooth Bleaching," J Oral Laser Applications, 2009, 9: 219-226.

Elliott, "Teeth Whitening, spot zapping, hair taming and even wrinkle erasing: so could BLUE technology be the future of beauty?" May 31, 2015, published online at http://www.dailymail.co.uk/femail/article-3099582/Teeth-whitening-spot-zapping-hair-taming-wrinkle-erasing-BLUE-technology-future-beauty.html.

Hirmer et al., "Spectroscopic study of human teeth and blood from visible to terahertz frequencies for clinical diagnosis of dental pulp vitality," J Infrared Mill Terahz Waves, 2012, 33:366-375.

Joiner et al., "Tooth colour: a review of the literature," J of Dentistry, 2003, 32: 3-12.

Spitzer et al., "The absorption and scattering of light in bovine and human dental enamel," Calcif. Tiss. Res. 1975, 17:129-137.

Bosch et al., "Optical properties of dentin," Chapter 3, Dentine and dentine reactions in the oral cavity, pp. 34-40, 1987.

Young et al., "A study of hydrogen peroxide chemistry and photochemistry in tea stain solution with relevance to clinical tooth whitening," J of Dentistry, 2012, Article in Press.

\* cited by examiner

ORAL TREATMENT DEVICE

BACKGROUND

Oral treatments, such as tooth whitening, are an increasingly popular treatment. Dentists and patients alike are searching for techniques that are both convenient and comfortable. Typically, to whiten a user's teeth a composition containing hydrogen peroxide is applied to the teeth and allowed to remain in contact with the teeth to be bleached for a period of time. Current systems are available that allow a user to apply radiation or light to the surfaces of the teeth that are pre-coated with the whitening composition to enhance the effectiveness of the whitening composition. However, currently available systems are bulky and rigid and undesirable for one or more reasons, such as requiring complex head mounting gear, being hand-held, or requiring a furniture-like mounted lamp. Specifically, current systems do not emit radiation or light onto the user's pre-coated teeth uniformly and in a manner that effectively covers the entire tooth surface. Thus, a need exists for a tooth whitening device that is able to effectively emit radiation or light onto a user's teeth.

BRIEF SUMMARY

The present invention may be directed, in one aspect, to a teeth whitening system that emits electromagnetic radiation, such as light, onto surfaces of the user's teeth.

In one aspect, the invention may be an oral treatment device comprising: an intraoral mouthpiece comprising: a lamp support structure comprising a lamp support surface having a concave curvature and a front surface having a convex curvature, the lamp support structure formed of a first material; a lamp comprising: a flexible sheet body having a front surface and a rear surface; and a plurality of light emitters embedded within the flexible sheet body that generate light which is emitted from the rear surface of the flexible sheet body; the lamp mounted to the lamp support surface of the lamp support structure so that the rear surface of the flexible sheet body of the lamp assumes a concave curvature, thereby forming a lamp assembly, the lamp operably coupled to a control circuit having a power source; and a guard component overmolded to the lamp assembly, the guard component formed of an elastomeric material having a hardness that is less than a hardness of the first material.

In another aspect, the invention may be an oral treatment device comprising: an intraoral mouthpiece comprising: a lamp support structure comprising a lamp support surface; first and second lamps, each of the first and second lamps comprising a plurality of light emitters that generate light which is emitted from a rear surface of the lamp; each of the first and second lamps mounted to the lamp support surface, thereby forming a lamp assembly, each of the first and second lamps operably coupled to a control circuit having a power source; and a lamp retaining component coupled to the lamp support structure, a lower portion of the first lamp and an upper portion of the second lamp retained between the lamp retaining component and the lamp support surface of the lamp support structure.

In yet another aspect, the invention may be an oral treatment device comprising: an intraoral mouthpiece comprising: a lamp support surface; first and second electrical contact elements electrically coupled to a control circuit having a power source, the first electrical contact element comprising a first contact surface and the second contact element comprising a second contact surface, each of the first and second contact surfaces of the first and second contact elements forming a portion of the lamp support surface; a lamp comprising: a plurality of light emitters that generate light which is emitted from a rear surface of the lamp; and first and second electrical contacts, the first electrical contact having a first contact surface that forms a first portion of a front surface of the lamp, and the second electrical contact having a second contact surface that forms a second portion of the front surface of the lamp; and the lamp mounted to the lamp support surface so that: (1) the first contact surface of the first electrical contact of the lamp contacts the first contact surface of the first electrical contact element; and (2) the second contact surface of the second electrical contact of the lamp contacts the second contact surface of the second electrical contact element.

In still another aspect, the invention may be an oral treatment device comprising: a control circuit comprising a power source; and an intraoral mouthpiece comprising: a first electrical conductor configured to have a first electrical charge, a second electrical conductor configured to have a second electrical charge that is opposite the first electrical charge, and a third electrical conductor configured to have the first electrical charge; first and second lamps, each of the first and second lamps comprising: a plurality of light emitters configured to generate light; and first and second electrical contacts; the first lamp positioned above the second lamp; and the first electrical conductor electrically coupling the power source to the first electrical contact of the first lamp, the third electrical conductor electrically coupling the power source to the first electrical contact of the third lamp, and the second electrical conductor coupling the power source to each of the second electrical contacts of the first and second lamps.

In a further aspect, the invention may be an oral treatment device comprising: an intraoral mouthpiece comprising: a lamp support structure having an upper edge, a lower edge, a first side edge, and a second side edge; a lamp comprising a plurality of light emitters configured to generate light which is emitted from the lamp, the lamp mounted to the lamp support structure to form a lamp assembly, the lamp operably coupled to a control circuit having a power source; and a guard component coupled to the lamp assembly, the guard component formed of an elastomeric material, the guard component comprising a first wing portion extending beyond the first side edge of the lamp support structure and a second wing portion extending beyond the second side edge of the lamp support structure, the first and second wing portions forming flexible distal end portions of the intraoral mouthpiece.

In a still further aspect, the invention may be an oral treatment device comprising: an intraoral mouthpiece comprising: a lamp comprising: a flexible sheet body having a front surface and a rear surface; and a plurality of light emitting diodes embedded within the flexible sheet body that generate light which is emitted from the rear surface of the flexible sheet body, the lamp operably coupled to a control circuit having a power source; and the flexible sheet body comprising: a flexible lens plate formed of a biocompatible material, the flexible lens plate having a front surface and a rear surface; and the plurality of light emitting diodes printed to the front surface of the flexible lens plate, the rear surface of the flexible lens plate forming the rear surface of the flexible sheet body; and the rear surface of the flexible sheet body of the lamp having a concave curvature and being exposed so as to form a light emitting surface of the mouthpiece.

In an even further aspect, the invention may be an oral treatment device comprising: an intraoral mouthpiece comprising: a first light emitting surface configured to emit light onto a user's maxillary teeth, the first light emitting surface having a concave curvature; a second light emitting surface configured to emit light onto a user's mandibular teeth, the second light emitting surface having a concave curvature; the first and second light emitting surface located on opposite sides of a horizontal reference plane; the first light emitting surface inclined so that a first acute angle is formed between with the first light emitting surface and the horizontal reference plane; and the second light emitting surface inclined so that a second acute angle is formed between with the second light emitting surface and the horizontal reference plane.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
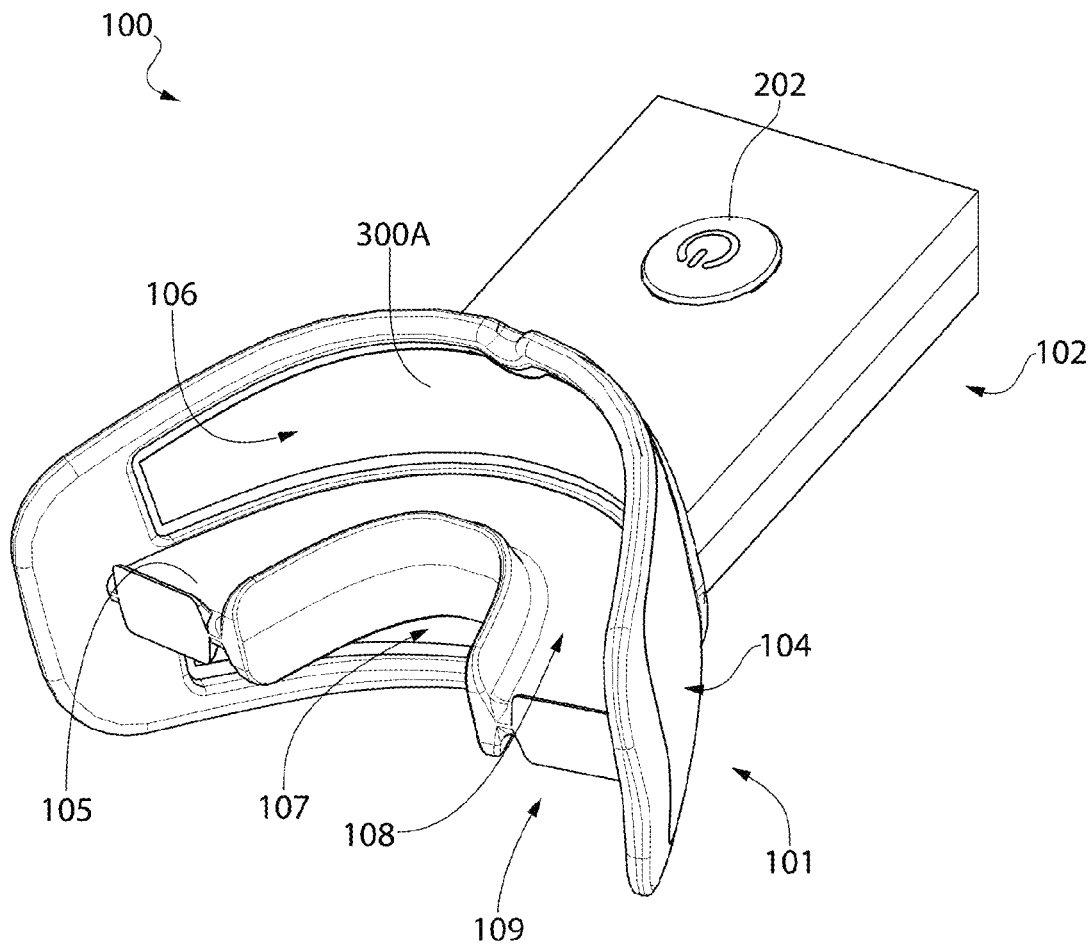
FIG. 1 is a rear perspective view of a teeth whitening device in accordance with a first embodiment of the present invention.
Figure 2:
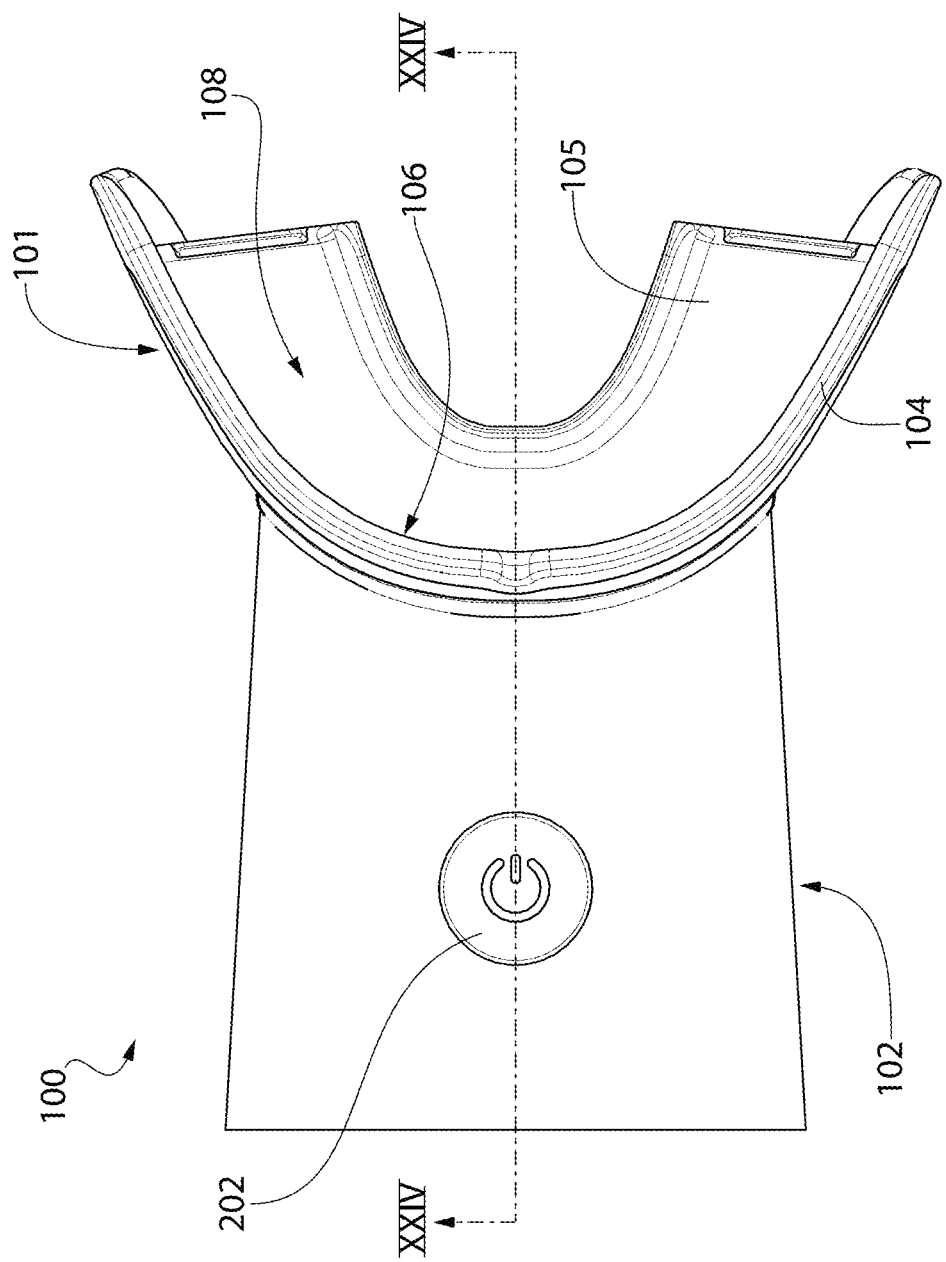
FIG. 2 is a top view of the teeth whitening device of FIG. 1.
Figure 3:
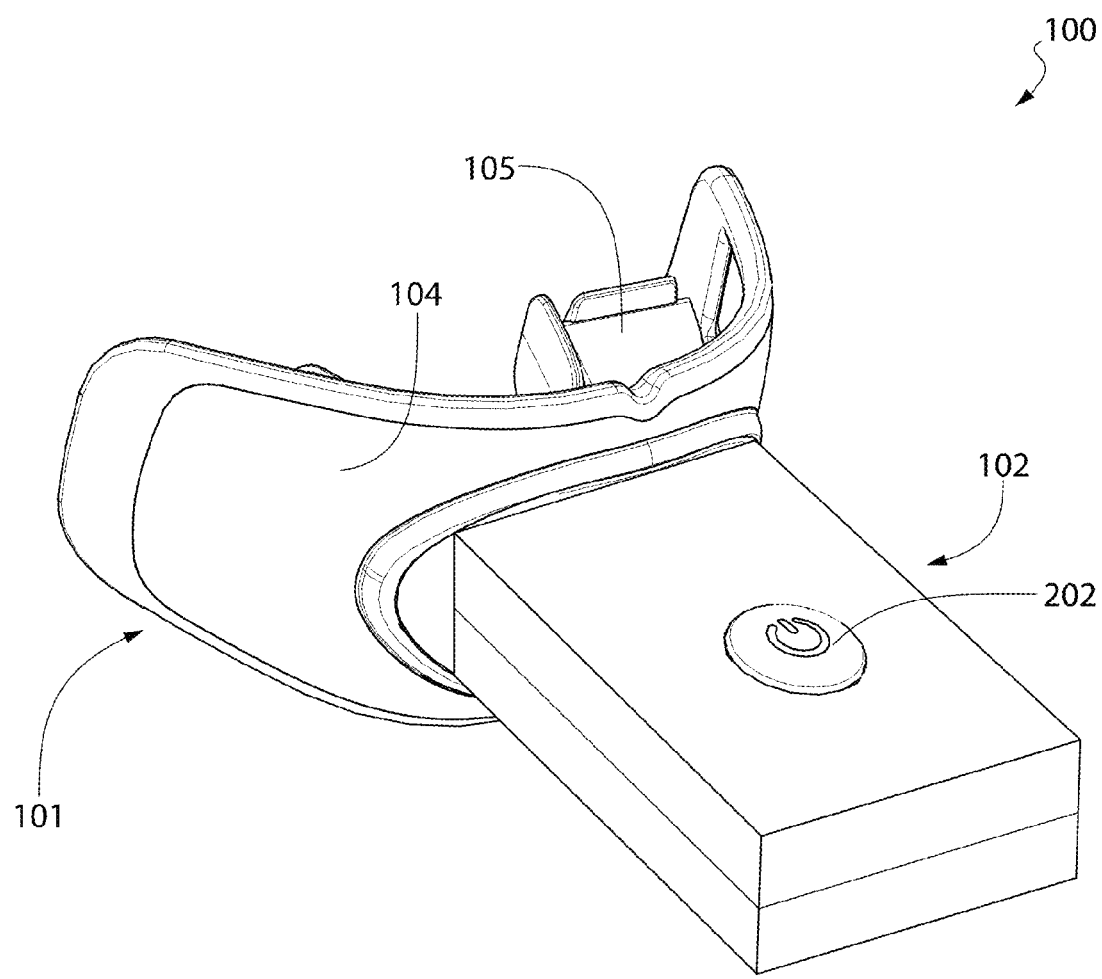
FIG. 3 is a front perspective view of the teeth whitening device of FIG. 1.
Figure 4:
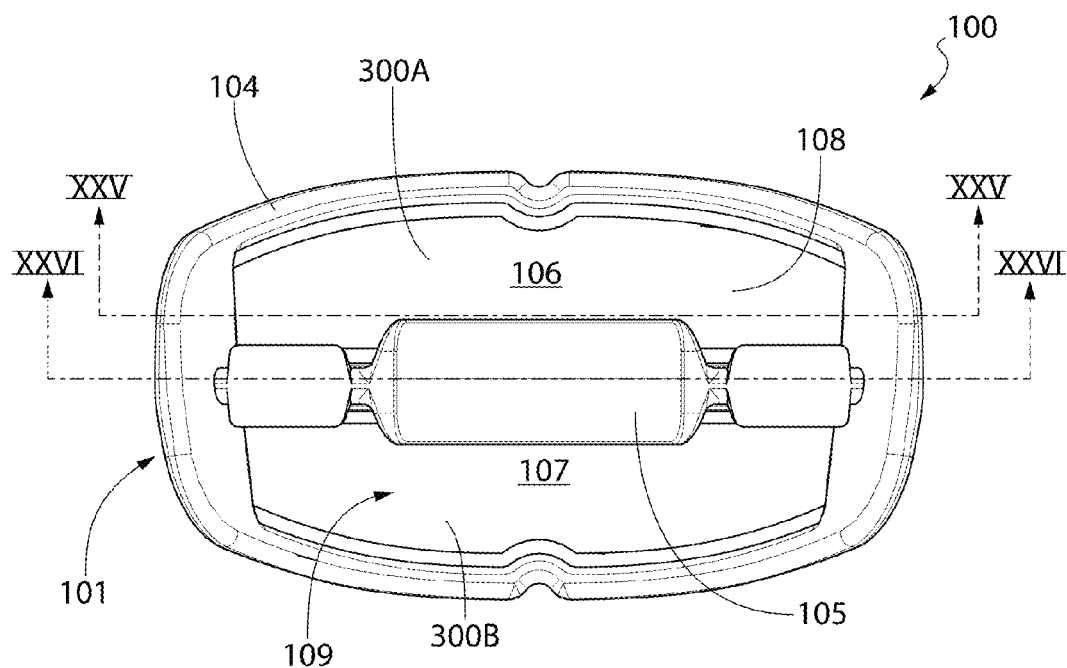
FIG. 4 is a rear view of the teeth whitening device of FIG. 1.
Figure 5:
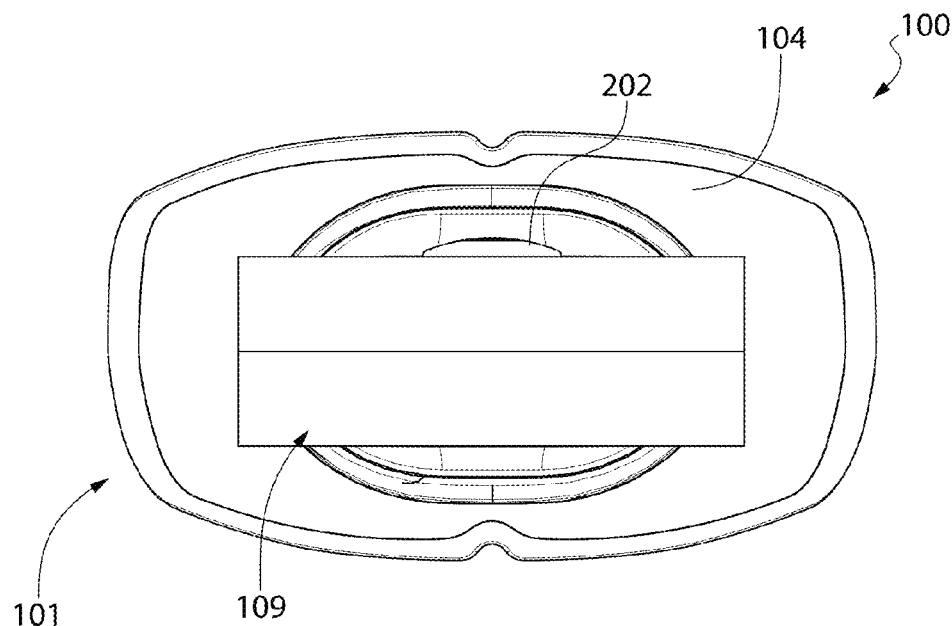
FIG. 5 is a front view of the teeth whitening device of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the illustrated embodiments. Accordingly, the invention expressly should not be limited to such exemplary embodiments illustrating some possible non-limiting combination of features that may exist alone or in other combinations of features; the scope of the invention being defined by the claims appended hereto.

Furthermore, it should be noted while the oral treatment device of the present invention is described herein as being a teeth whitening device, it is to be understood that the invention is not so limited. For example, in certain embodiment, the oral treatment device of the present invention can be configured to emit light for other oral treatment purposes, including without limitation, enhancing oral tissue healing, antibacterial purposes, treating tooth sensitivity, disinfecting, cleansing, and combinations thereof. In such other embodiments, the characteristics of the light being emitted by the oral treatment device of the present invention will be selected to achieve the desired treatment, such as wavelength, intensity, power, light density and/or other characteristics. In still other embodiments, the benefit of the oral treatment device can be dictated by the oral car material with which it is used in conjunction therewith. For example, in certain embodiments, the oral care treatment device may be used in conjunction with other oral care materials, including without limitation, antibacterial agents, anti-sensitivity agents, anti-inflammatory agents, anti-attachment agents, plaque indicator agents, flavorants, sensates, breath freshening agents, gum health agents and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, minerals, hydrogen peroxide, urea peroxide, sodium percarbonate, PVP-H2O2, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, *sassafras* oil, clove oil, sage oil, *eucalyptus* oil, marjoram oil, cinnamon oil, lemon oil, lime oil, grapefruit oil, and/or orange oil.

Referring to FIGS. 1-5 concurrently, a teeth whitening device 100 will be described in accordance with an embodiment of the present invention. As will be described in greater detail below, the teeth whitening device 100 is configured to emit electromagnetic radiation, in the form of light, that assists with the whitening of teeth. The teeth whitening device 100, in some embodiments, can be used by itself to whiten the teeth of the user by simply generating light that is emitted onto the facial surfaces of the users teeth. In certain other embodiments, however, the teeth whitening device 100 may be used in conjunction with a tooth whitening composition. Suitable tooth whitening compositions include, but are not limited to, hydrogen peroxide compositions, carbamide peroxide compositions, calcium peroxide compositions, sodium perborate compositions, combinations thereof, or any other oral care material that is known or discovered to whiten teeth. In such embodiments, the tooth whitening composition can be applied directly to the desired surfaces of the user's teeth (such as the facial surfaces) or can be applied to the teeth whitening device 100 itself. Either way, the tooth whitening composition comes into contact with the user's teeth while the light emitted from the teeth whitening device 100 is concurrently passed through the tooth whitening composition to irradiate the teeth.

Furthermore, while in the illustrated embodiment the invention is shown such that the light is emitted from the teeth whitening system 100 to contact the buccal surfaces of the teeth, in other embodiments the teeth whitening system 100 can be configured to emit light onto the lingual, incisal, and/or occlusal surfaces of the teeth instead of and/or in addition to the buccal surfaces. In such embodiments, the lamps can be positioned within the bite plate and/or in the rear walls of the mouthguard that oppose the lingual surfaces of the teeth.

The teeth whitening system 100 generally comprises a mouthpiece 101 and a housing 102. In the illustrated embodiment, the mouthpiece 101 is sized and shaped so that it can be inserted into the user's oral cavity during use and, thus, can be considered to be intraoral in nature. To the contrary, the housing 102 is sized, shaped, and oriented so that it protrudes from the user's oral cavity during use of the teeth whitening system 100 and, thus, can be considered extraoral in nature. In one embodiment, the housing 102 and the mouthpiece are configured such that the teeth whitening system 100 is a self-contained hands-free device that can put into the oral cavity and supported in the user's mouth simply using one's teeth.

The housing 102 and the mouthpiece 101 are coupled together so that the mouthpiece 101 extends from the housing 102 in a direction generally opposite the direction in which light is emitted from the mouthpiece 101. The mouthpiece 101 (which as discussed below may be formed by a plurality of components) generally comprises a body that includes an arch-shaped wall 104 and a bite platform 105 extending horizontally from the arch-shaped wall 104. The arch-shaped wall 104 has a curvature that generally corresponds to the arch of the human dentiture.

The arch-shaped wall 104 comprises a first light emitting surface 106 that is located above the bite platform 105 and a second light emitting surface 107 that is located below the bite platform 105. The first light emitting surface 106 has a concave curvature and is configured to emit light onto a user's maxillary teeth. The second light emitting surface 107 also has a concave curvature and is configured to emit light onto a user's mandibular teeth. In the illustrated embodiment, the light emitted by the first and second light emitting surfaces 106, 107 is generated by first and second flexible lamps respectively, the details of which will be described in greater detail below with respect to FIGS. 6-7 and 17-19. In other embodiments, however, the light emitted by the first and second light emitting surfaces 106, 107 may be generated with other light sources that are either embedded in the arch-shaped wall 104 and/or transmitted to the first and second light emitting surfaces 106, 107 using light piping or other suitable techniques. As will be discussed in greater detail below, the first and second light emitting surfaces 106, 107 are positioned and oriented within the mouthpiece 101 to be positioned close to and optimally oriented relative to the user's maxillary and mandibular teeth when the teeth whitening system 100 is being used.

The arched wall 104 and the bite platform 105 collectively form a first channel 108 and a second channel 109 for receiving a user's teeth during a tooth whitening session. More specifically, in the illustrated embodiment, an upper portion of the arched wall 104 comprises the first light emitting surface 106 and extends upward from an upper surface of the bite platform 105, thereby forming the first channel 108. A lower portion of the arched wall 104 comprises the second light emitting surface 107 and extends downward from a lower surface of the bite platform 105, thereby forming the second channel 109. During use, the mouthpiece 101 is inserted into a user's mouth such that the bite platform 105 is trapped or sandwiched between the user's maxillary and mandibular teeth. When so positioned, the first light emitting surface 106 is adjacent to the facial surfaces of the user's maxillary teeth and has a curvature such that the first light emitting surface 106 generally corresponds to at least the anterior portion of the arch of the maxillary teeth. Similarly, the second light emitting surface 107 is adjacent the facial surfaces of the user's mandibular teeth and has a curvature such that the second light emitting surface 107 generally corresponds to at least the anterior portion of the arch of the mandibular teeth.

It should be noted, however, that in certain embodiments of the invention, the mouthpiece 101 may be designed such that the bite platform 105 is omitted. In one such embodiment, the first and second light emitting surfaces 106, 107 may be maintained as separate and distinct light emitting areas, each of which emits light only onto the facial surfaces of the maxillary teeth and the facial surfaces of the mandibular teeth respectively. In another such embodiment, the first and second light emitting surfaces 106, 107 may be merged into a single light emitting area that emits light onto the facial surfaces of both the maxillary and mandibular teeth. In another embodiment, the bite platform 105 may be omitted and only a single light emitting surface may be provided that emits light only onto the facial surfaces of the maxillary teeth or only onto the facial surfaces of the mandibular teeth at any given time. In still another embodiment, the bite platform 105 can be included and only one of the first or second light emitting surfaces may be provided. In a further embodiment, the mouthpiece 101 may be formed as two separable components, wherein one component contains the first light emitting surface 106 for emitting light onto the upper teeth and the other component contains the second light emitting surface 107 for emitting light onto the user's lower teeth.

In certain embodiments, the mouthpiece 101 (including all of the components thereof that come into contact with the oral cavity) is formed of a biocompatible material, such as a food grade polymer. Suitable biocompatible materials include, without limitation, polyethylene terephthalate (PET), polypropylene (PP), polyethylene naphthalate (PEN), polyethylene (PE), silicone, ethylene propylene diene monomer (EPDM), polycarbonate (PC), thermoplastic elastomers (TPE), and other plastics. Of course, the invention is not to be so limited in all embodiments and other materials are possible for construction of the mouthpiece 101, and various components thereof. In certain embodiments, the mouthpiece 101, or at least portions thereof, may be formed of an elastomeric material. This will be described in greater detail below.

Figure 25:
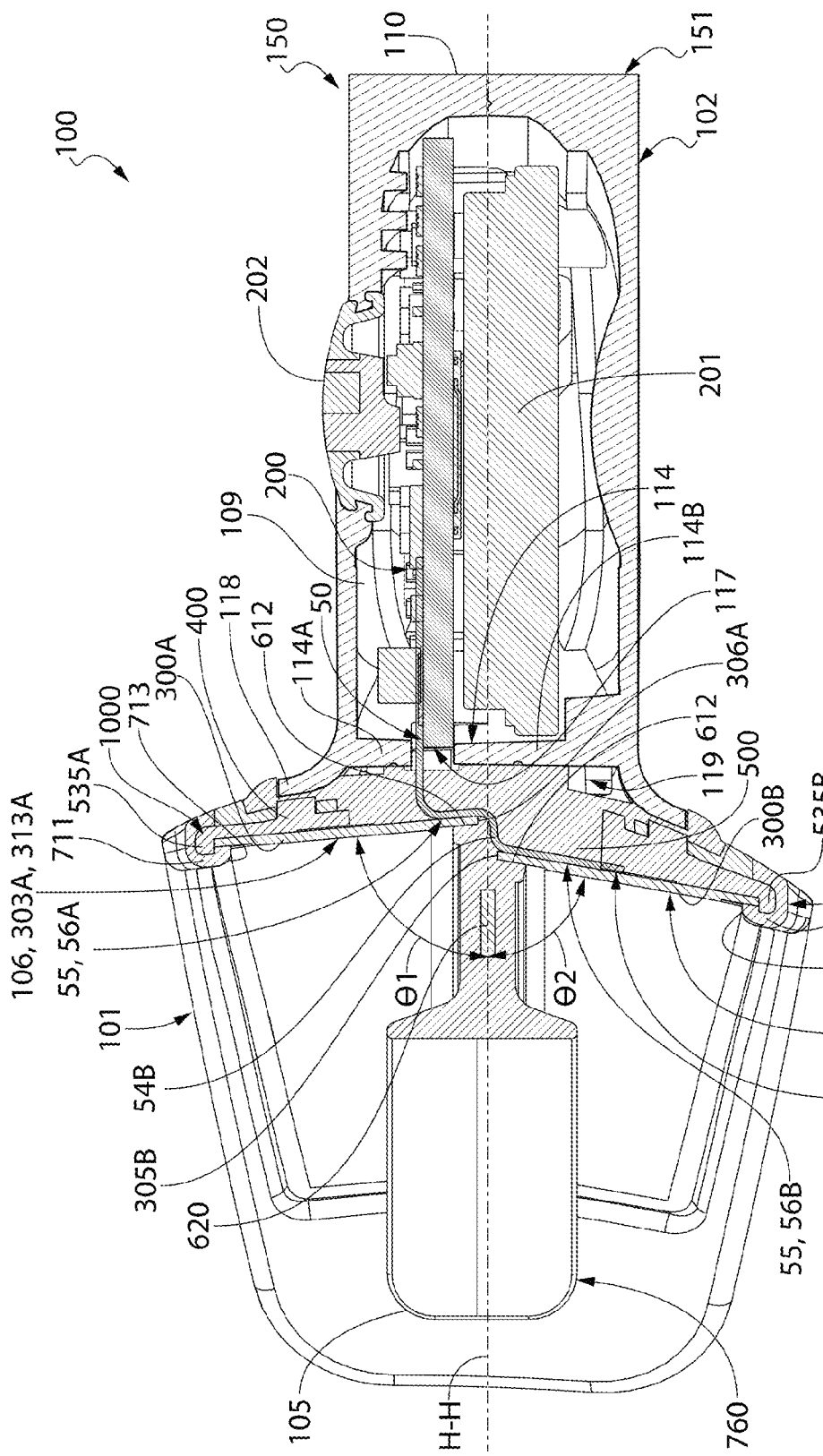
FIG. 25 is a cross-sectional view of the teeth whitening device of FIG. 1 taken along view XXIV of FIG. 2.

In the illustrated embodiment, the housing 102 contains a control circuit 200 (see FIG. 25). The control circuit 200 generally comprises, among other components, a properly programmed processor, a memory device, a power source 201, a timer, and an actuator 202 that are operably coupled together. The control circuit 200, in turn, is operably and electrically coupled to each of the first and second lamps 300A-B so that the control circuit 200 can control the operation thereof.

The properly programmed processor may be any suitable microprocessor based programmable logic controller, personal computer, or the like that has memory for storing various instructions to control the operation of the first and second lamps 300A-B. The processor is programmed with algorithms to receive data from the various other electrical components and sensors, analyze the data, and cause the electrical components to operate in a desired or predetermined manner based on instructions that are stored in the memory device or an integrated memory area of the processor.

In the illustrated embodiment, the power source 201 is operably and electrically coupled to the processor and to the first and second lamps 300A-B so that electrical energy can be provided thereto for powering the same. The power source 201 may be one or more batteries, battery cells, printed batteries, rechargeable batteries, super capacitors, or a control circuit that stores electrical energy. Alternatively, in certain embodiments, the power source may be omitted and instead the electronic components of the tooth whitening device 100 may be powered by a plug that is coupled to a power supply, such as a wall socket. While not shown herein, the teeth whitening device 100 may be part of a larger system that includes a docking station that includes charging capabilities. In one such embodiment, the teeth whitening device 100 is part of a system including docking station that includes a charging circuit configured to charge a rechargeable battery of the teeth whitening device 100 by inductive charging.

In the illustrated embodiment, the actuator 202 is a depressible button. However, the invention is not to be so limited and the actuator 202 can be any type of device that upon actuation powers on and/or off one or more of the electrical components stored within the housing 102. For example, the actuator 202 can be a slide switch, a touch pad, a knob, or any other component that upon actuation causes the teeth whitening device 100 to function as described herein. In other embodiments, the actuator 202 can be a sensor or other device that is automatically activated upon the mouthpiece 101 of the teeth whitening device being inserted into the oral cavity, such as a temperature sensor, a water-activated sensor that is activated by saliva, a proximity sensor, a humidity sensor, or any other suitable sensor or switch.

The actuator 202 is operably coupled to the processor so that upon depressing or otherwise actuating the actuator 202, the processor initiates operation of the teeth whitening system 100 as described in more detail below.

Figure 6:
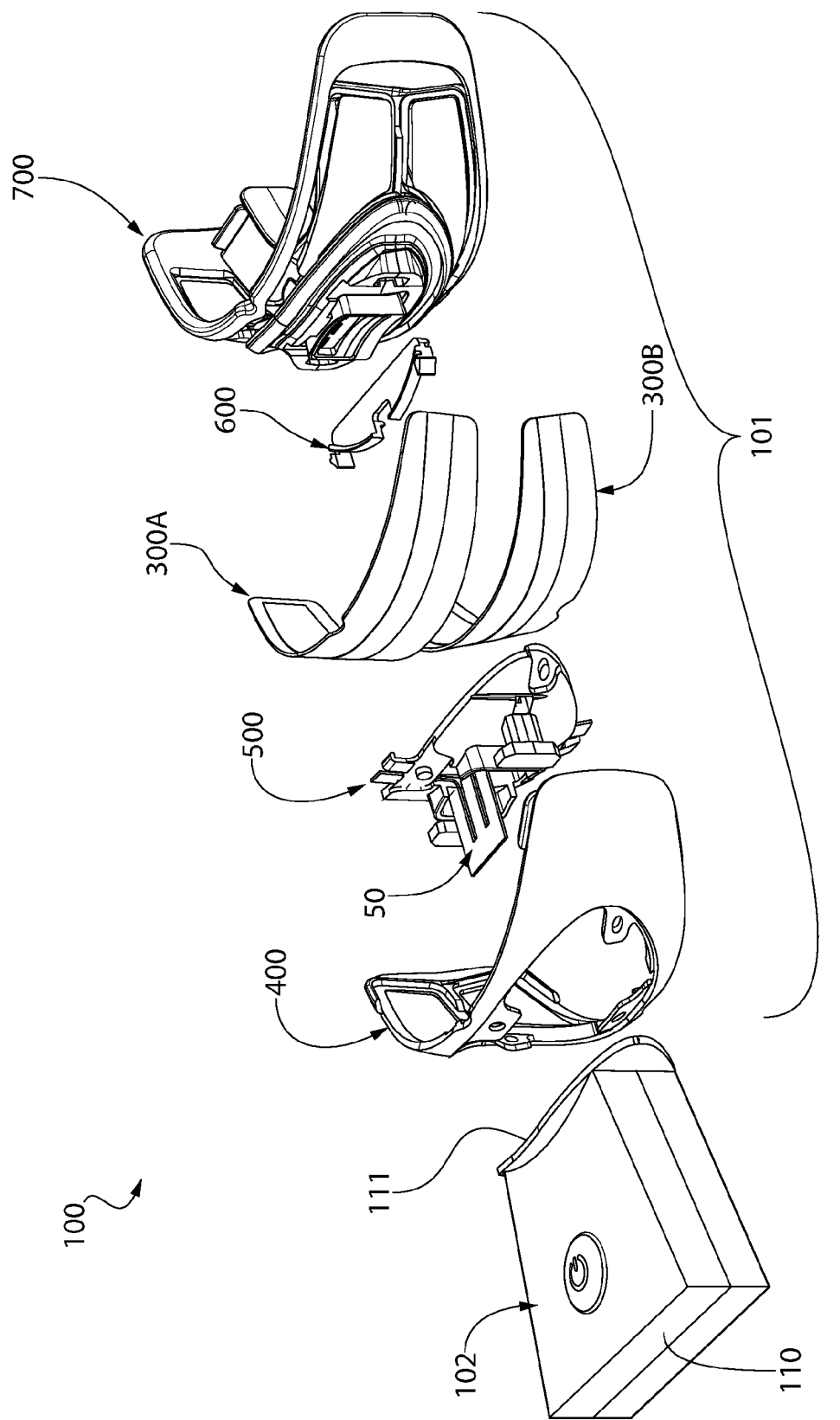
FIG. 6 is an exploded view of the teeth whitening device of FIG. 1, taken from a front perspective view thereof.
Figure 7:
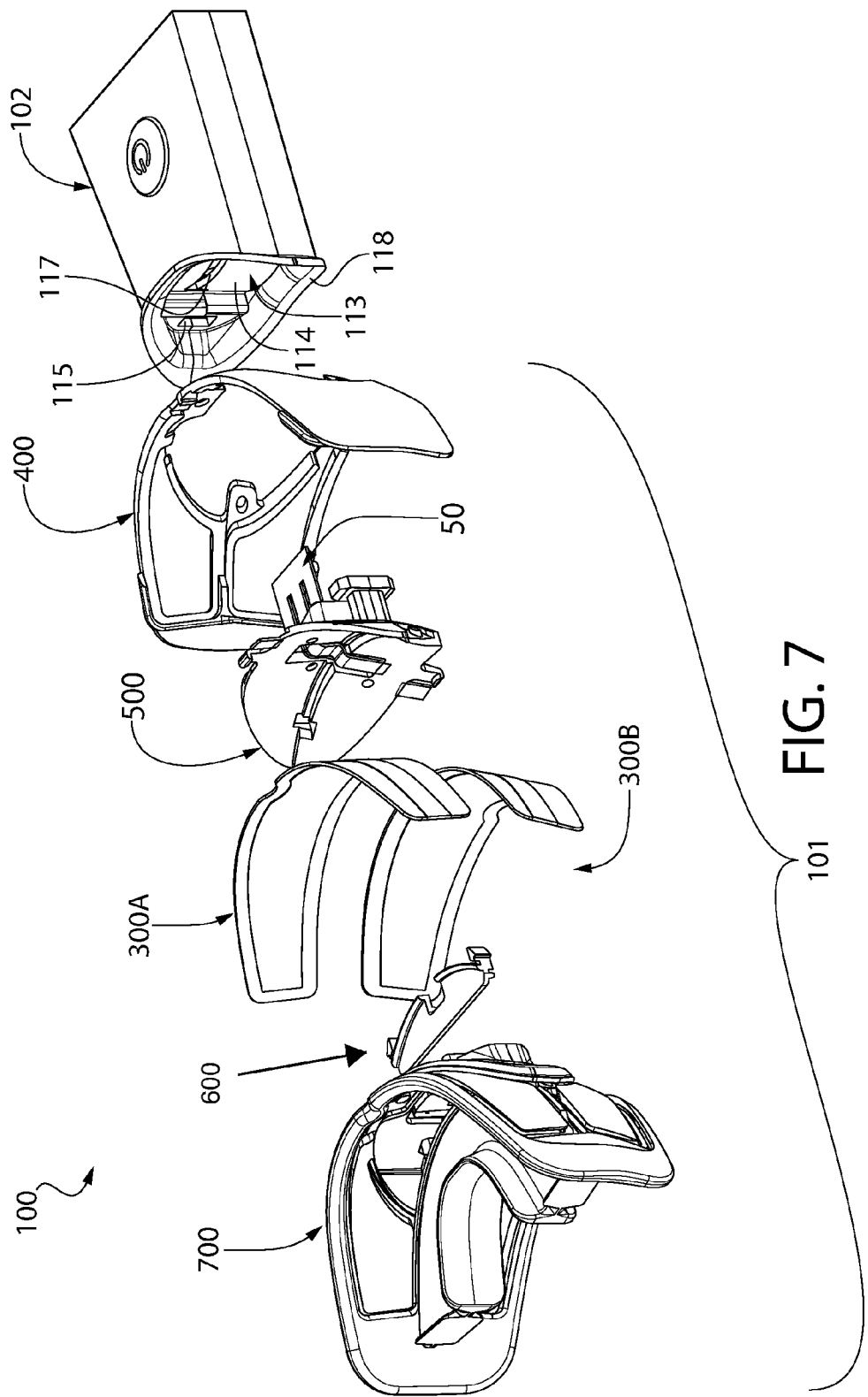
FIG. 7 is an exploded view of the teeth whitening device of FIG. 1, taken from a rear perspective view thereof.
Figure 8:
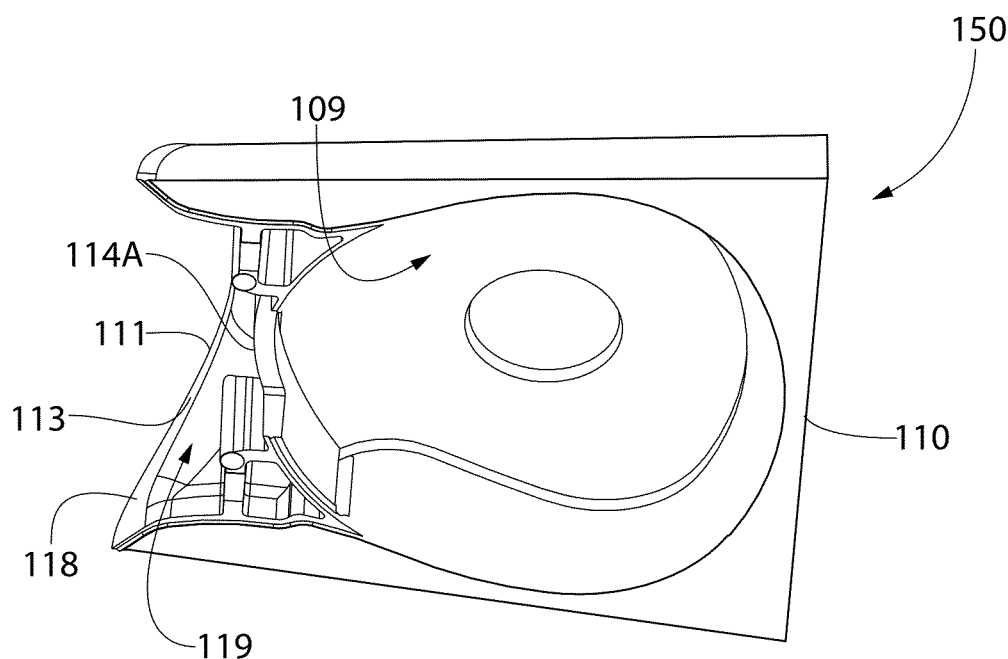
FIG. 8 is a bottom perspective view of the upper portion of the housing of the teeth whitening device of FIG. 1.
Figure 9:
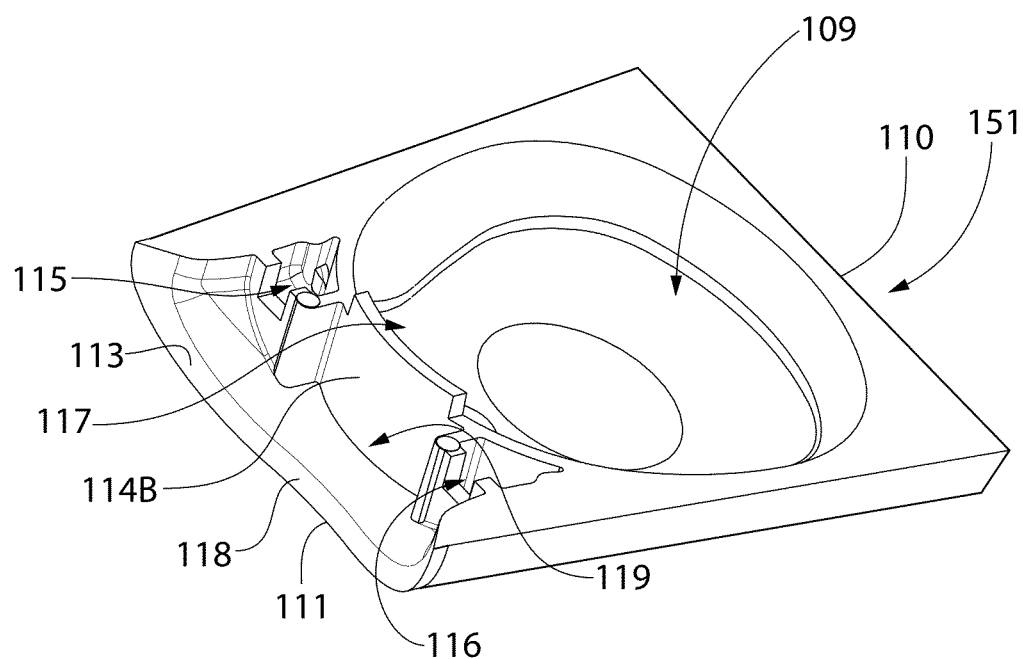
FIG. 9 is a top perspective view of the lower portion of the housing of the teeth whitening device of FIG. 1.

Referring now to FIGS. 6-7 concurrently, the teeth whitening device 100 is illustrated in an exploded state. As can be seen, in the illustrated embodiment, the mouthpiece 101 of the teeth whitening device 100 is a multi-component structure that generally comprises a curved support plate 400, an anchor component 500, an electrical contact component 50, first and second flexible lamps 300A-B, a lamp retaining component 600, and a guard component 700. In other embodiments, one or more of the aforementioned components may be omitted and in even further embodiments, the mouthpiece 101 may simply comprises single component to which at least one of the first or second lamps 300A-B is mounted as discussed below. The first and second flexible lamps 300A-B can be electrically coupled to the control circuit 200 in series or in parallel.

Referring now to FIGS. 6-9 and 24-26 concurrently, the housing 102 generally comprises an upper portion 150 and a lower portion 151. When joined, the upper and lower portions 150, 151 of the housing 150 form an internal chamber 109 in which the electrical components of the control circuit 200 are disposed. When the teeth whitening device 100 is assembled, the internal chamber 109 is sealed so as to prevent the ingress of water and other fluids. The housing 102 can be formed of any suitable materials, including hard plastics such as PP or any other hard plastic material described herein. If desired, an elastomeric material, such as a thermoplastic elastomer, can be overmolded to the upper and lower portions 150, 151 of the housing 102. Such overmolding can be used to seal the interface between the upper and lower portions 150, 151 of the housing 102 and/or to provide a gripping surface to the user.

The housing 101 extends from a proximal end 110 to a distal end 111. The distal end 111 is configured to have the mouthpiece 101 coupled thereto. In the illustrated embodiment, the distal end 111 of the housing is flared and comprises an opening 113 through which the mouthpiece 101 extends for mounting to the housing 102. The opening 113 is defined by a closed-geometry edge 118 of the distal end 111 of the housing 102. The opening 113 forms a passageway into a mounting chamber 119. The mounting chamber 119 terminates in a housing wall 114. The housing wall 114 separates the mounting chamber 119 of the housing 102 from the internal chamber 109 of the housing 102. The housing wall 114 comprises a first anchor aperture 115, a second anchor aperture 116, and an electrical connection aperture 117. The housing wall 114 is formed by the combination of an upper wall portion 114A that is part of the upper portion 150 of the housing 102 and a lower wall portion 114B that is part of the lower portion 151 of the housing 102.

As will be described in greater detail below, the first and second anchor apertures 115, 116 provide a feature through which the anchor elements 521A-B of the mouthpiece 101 extend, thereby allowing the anchor elements 521A-B to mechanically mate with the housing 101 to fix the mouthpiece 110 to the housing 102. Moreover, the electrical connection aperture 117 forms a passageway from the mounting chamber 119 into the internal chamber 109 so that electrical conductors (discussed in greater detail below) can be run that electrically couple the control circuit 200 to the first and second lamps 300A-B, thereby providing a mechanism through which electrical power from the power source 201 can be provided to the first and second lamps 300A-B.

Figure 10:
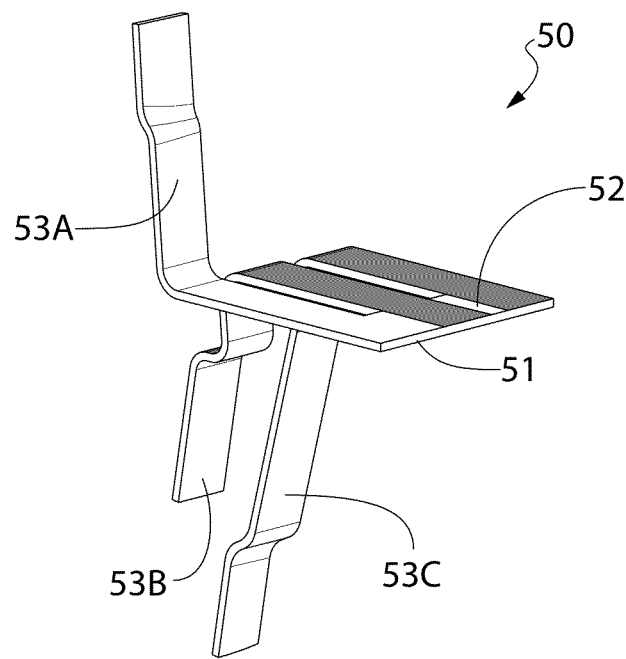
FIG. 10 is a front perspective view of the electrical contact component of the teeth whitening device of FIG. 1.
Figure 11:
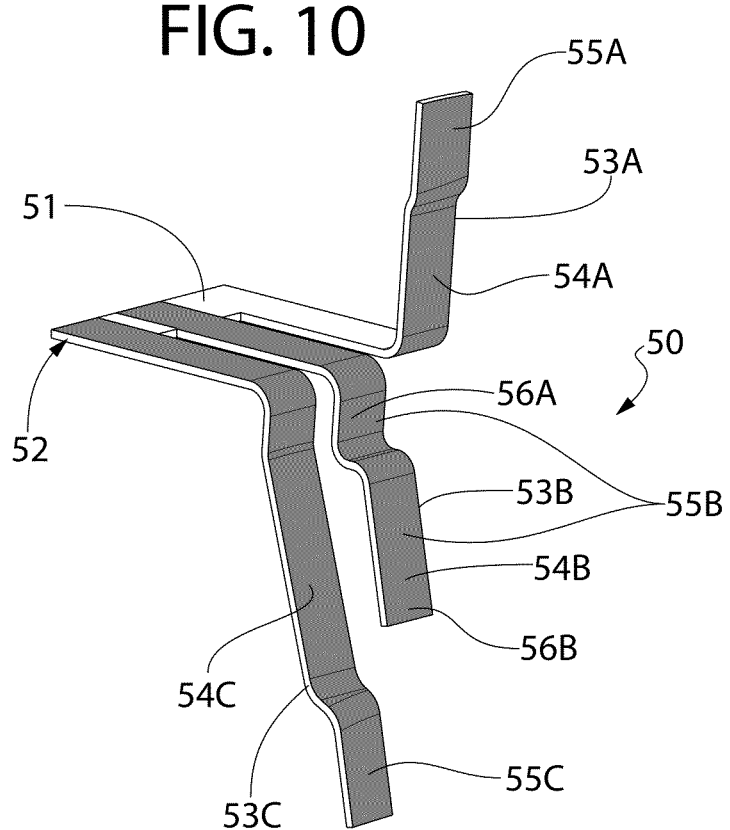
FIG. 11 is a rear perspective view of the electrical contact component of the teeth whitening device of FIG. 1.

Referring now to FIGS. 10-11, an electrical contact component 50 is illustrated according to an embodiment of the present invention. As will be described in greater detail below, the electrical contact component 50 is mounted within the mouthpiece 101 and is configured to provide the necessary electrical energy from the power source 201 to each of the flexible lamps 300A-B so that the flexible lamps 300A-B can be activated.

The electrical contact component 50 generally comprises an integrally formed monolithic base structure 51 formed of a dielectric material. The base structure 51 comprises a base section 52 and first, second, and third tabs 53A-C extending from the base section 52. Each of the first, second and third tabs 53A-C are elongated in nature and extend parallel to one another in a spaced apart manner. Each of the first, second, and third tabs 53A-C are provided with an electrically conductive material, thereby converting each of the first, second, and third tabs 53A-C into first, second, and third electrical contact elements 54A-C respectively. The electrically conductive material may in the form of a metallic coating layer, an embedded metallic trace, an embedded wire, or combinations thereof.

Each of the first, second, and third electrical contact elements 54A-C are electrically isolated from one another in one embodiment. In another embodiment, the first and third electrical contact elements 54A, 54C may be in electrical communication due to the first and third electrical contact elements 54A, 54C carrying the same electrical charge when coupled to the control circuit 200. However, in such an embodiment, the first and third electrical contact elements 54A, 54C would still be electrically isolated from the second electrical contact element 54B, which carries an electrical charge that is opposite that which is carried by the first and third electrical contact elements 54A, 54C when coupled to the control circuit 200.

The first electrical contact element 54A comprises a first contact surface 55A. The second electrical contact element 54B comprises a second contact surface 55B. The third electrical contact element 54C comprises a third contact surface 55C. In the illustrated embodiment, the second contact surface 55B is a stepped surface comprising a first portion 56A and a second portion 56B that are horizontally offset from one another. As discussed below, the first portion 56A of the second contact surface 55B contacts a second electrical contact 312A of the first flexible lamp 300A while the second portion 56B of the second contact surface 55B contacts a second electrical contact 312B of the second flexible lamp 300B. The first contact surface 55A, on the other hand, contacts only the first electrical contact 311A of the first flexible lamp 300A, while the third contact surface 55C contacts only the first electrical contact 311B of the second flexible lamp 300B. In other embodiments, the second contact surface 55B may not be stepped and may simply be designed to contact a single electrical contact of one of the first or second lamps 300A-B.

It should further be noted that in certain embodiments, the first, second, and third electrical contact elements 54A-C can be separate and distinct structures. In one such embodiment, each of the first, second, and third electrical contact elements 54A-C can be tabs that are separately mounted within the mouthpiece. In still other embodiments, electrical energy can be supplied to the first and second lamps 300A-B through simple electrical conductors, such as wires and/or trace lines that are embedded within the mouthpiece 101. In such an embodiment (as is the case with the above illustrated embodiment), the first electrical conductor is configured to have a first electrical charge, the second electrical conductor is configured to have a second electrical charge that is opposite the first electrical charge, and the third electrical conductor is configured to have the first electrical charge.

Figure 12:
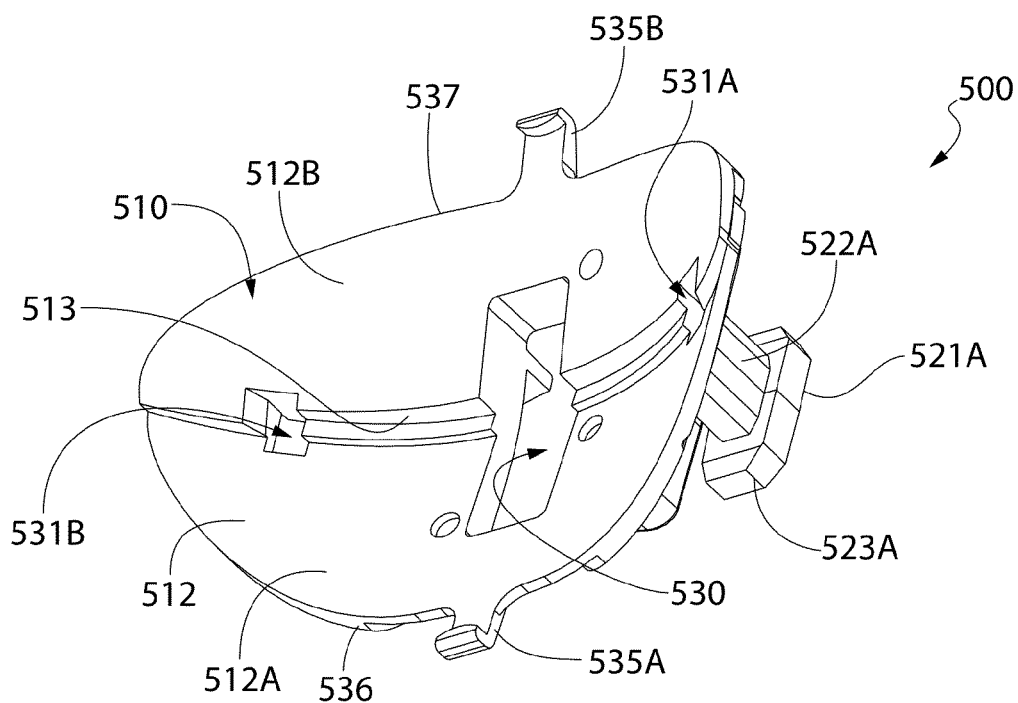
FIG. 12 is a rear perspective view of the anchor component of the teeth whitening device of FIG. 1.
Figure 13:
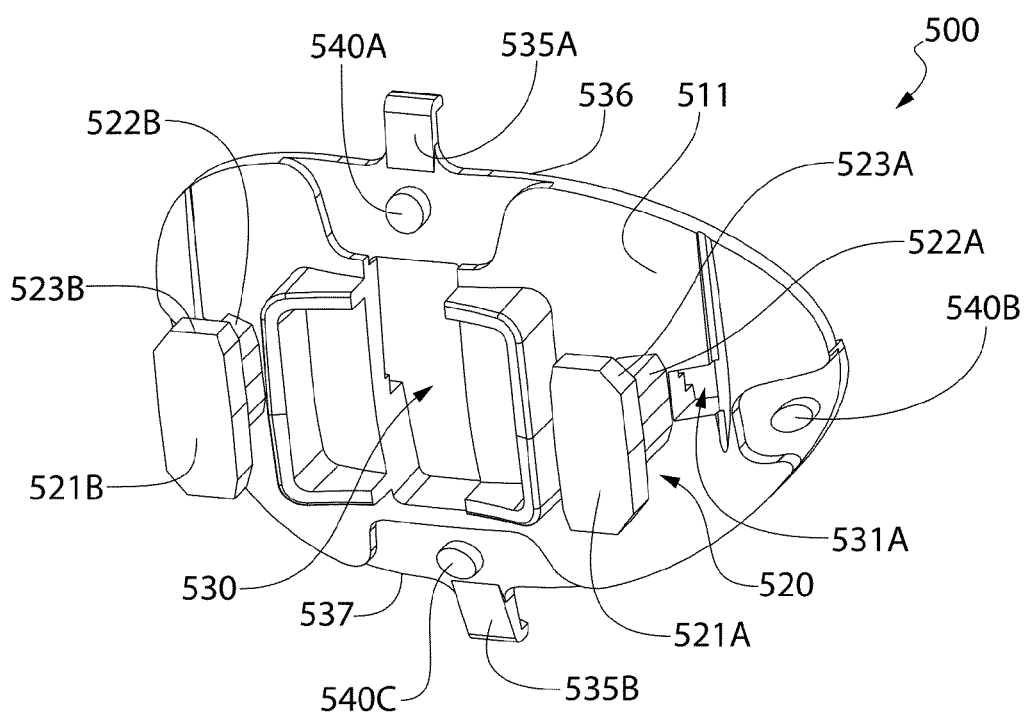
FIG. 13 is a front perspective view of the anchor component of the teeth whitening device of FIG. 1.
Figure 24:
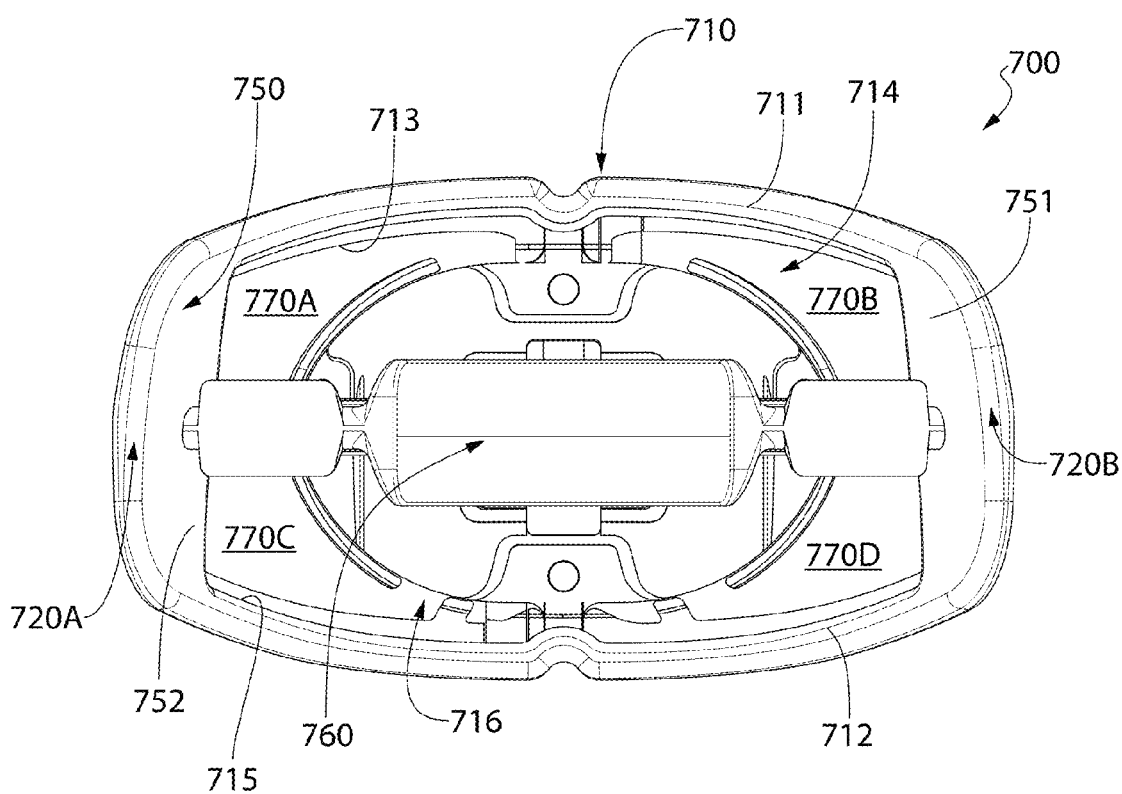
FIG. 24 is a rear view of the guard component of the teeth whitening device of FIG. 1.

Referring now to FIGS. 12-13 and 24 concurrently, an anchor component 500 is illustrated in accordance with an embodiment of the present invention. The anchor component 500 generally comprises a curved plate section 510 and an anchor section 520. The anchor section 520 protrudes from a front surface 511 of the curved plate section 510. The curved plate section 510 further comprises a rear surface 512 which, as discussed below, forms a portion of a lamp mounting surface when the anchor component 500 and curved support plate 400 are assembled. The rear surface 512 of the curved plate section 510 has a concave curvature. In one embodiment, the concave curvature of the curved plate section 510 is selected to generally correspond to the arch of a user's denture, and specifically to the anterior-most portion of said denture arch.

In the illustrated embodiment, the rear surface 512 of the curved plate section 510 is a stepped surface comprising a first surface portion 512A, a second surface portion 512B, and a tread surface portion 513 extending between the first and second surface portions 512A-B. As discussed in greater detail below, the first surface portion 512A and the second surface portion 512B are horizontally offset from one another so that the first and second lamps 300A-B can be mounted within the mouthpiece 101 in a desired offset and inclined orientation.

The anchor portion 520 of the anchor component provides a mechanism by which the mouthpiece 101 can be mounted to the housing 102, as is discussed in greater detail below. In the illustrated embodiment, the anchor portion 520 comprises first and second anchor elements 521A, 521B. In other embodiments, a single anchor element can be utilized to achieve fixation of the mouthpiece 101 to the housing 102. Each of the anchor elements 521A-B is illustrated as a peg member having a post portion 522A-B and a head portion 523A-B. For each of the anchor elements 521A-B, the head portion 523A-B has an enlarged cross-section as compared to the post section 522A-B, thereby forming a flange (or shoulder) at the end of the post portion 522A-B. As will be described in greater detail below, this flange (or shoulder) facilitates mechanical mating of the anchor elements 521A-B to the housing wall 114.

The curved plate section 510 of the anchor component 500 further comprises a central aperture 530. The central aperture 530 provides a passageway through the curved plate section 510 through which the second electrical contact element 54B extends when the mouthpiece 101 is assembled. The curved plate section 510 further comprises first and second locking apertures 531A-B for receiving snap-fit tabs 630A-B of the lamp retaining component 600 (discussed in greater detail below). The locking apertures 531A-B are located along a horizontal centerline of the anchor component 500 which, in the illustrated embodiment extends along the tread surface portion 513.

The anchor component 500 further comprises first and second lamp retaining features 535A-B. In the illustrated embodiment, the first and second lamp retaining features 535A-B are in the form of angled protuberances that protrude from the upper and lower edges 536, 537 of the curved plate section 510, respectively. As described below, the first retaining feature 535A is provided to engage an edge of the first flexible lamp 300A while the second retaining feature 535B is provided to engage an edge of the second flexible lamp 300B. In certain embodiments wherein the mouthpiece may include only a single flexible lamp, the anchor component 500 may be formed such that the first and second lamp retaining features 535A-B engage opposite edges of the same flexible lamp. Moreover, in certain embodiments, the rear surface 512 may not be stepped but rather a continuous and smooth surface.

Figure 28:
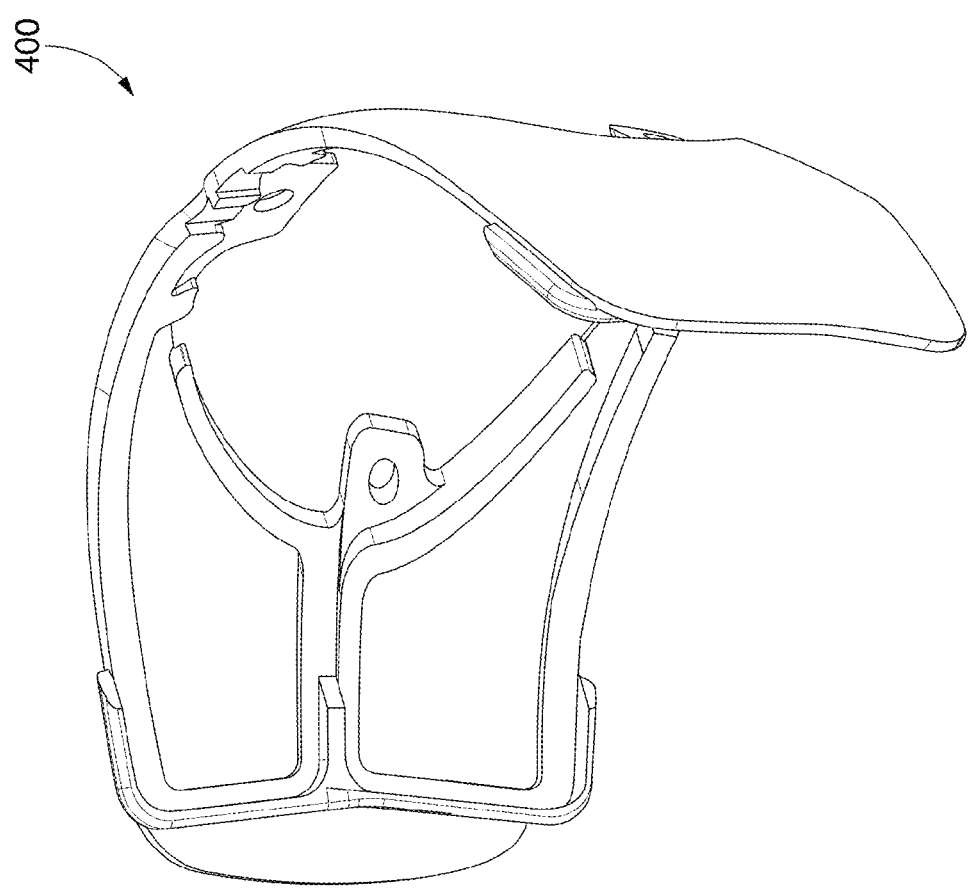
FIG. 28 is a rear perspective view of the curved support plate.

The anchor component 500 further comprises a plurality of protuberances 540A-D protruding from the front surface 511 of the curved plate section 510. The protuberances 540A-D are provided as mechanisms to ensure proper alignment and coupling between the anchor component 500 and the curved support plate 400 when these two components are coupled together to collectively form a lamp support structure 1000 (see FIG. 28). In certain embodiments, the anchor component 500 is formed of a rigid material, such as PP.

Figure 14:
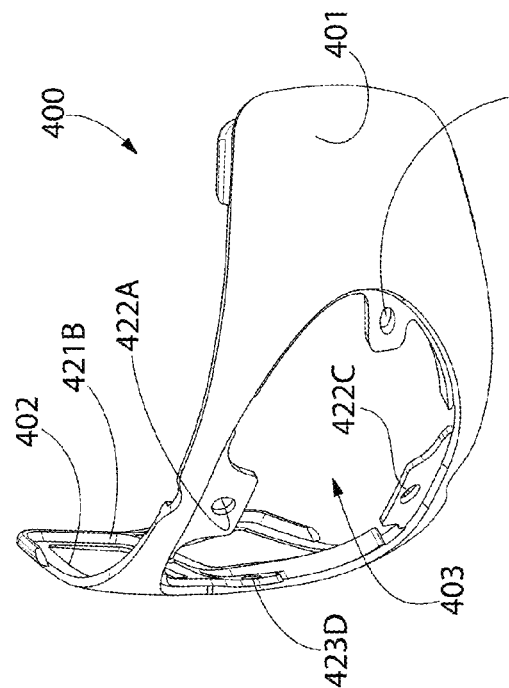
FIG. 14 is a rear perspective view of the curved support plate of the teeth whitening device of FIG. 1.
Figure 15:
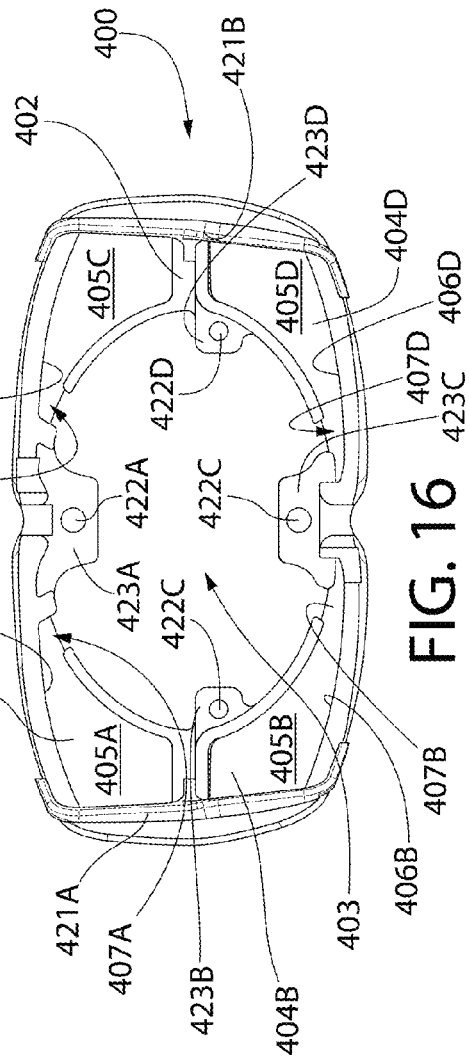
FIG. 15 is a front perspective view of the curved support plate of the teeth whitening device of FIG. 1.
Figure 16:
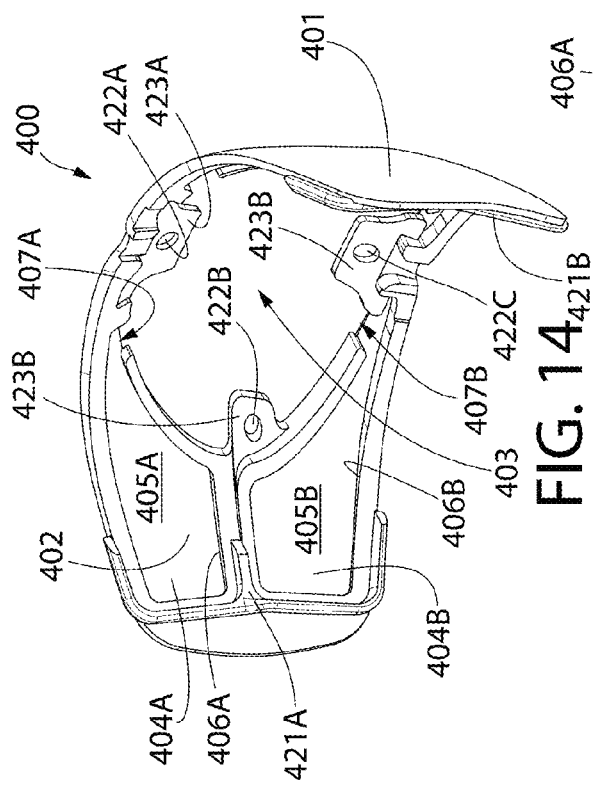
FIG. 16 is a rear view of the curved support plate of the teeth whitening device of FIG. 1.

Referring now to FIGS. 14-16 concurrently, a curved support plate 400 is illustrated in accordance with an embodiment of the present invention. The curved support plate 400, in combination with the anchor component 500, provides a lamp support structure 1000 that provides a degree of structural rigidity to the mouthpiece 101 for the flexible lamps 300A-B, especially during the manufacturing process. The curved support plate 400 is a thin curved plate structure having a front surface 401 and a rear surface 402. In certain embodiments, the curved support plate 400 is formed of a rigid material, such as a hard plastic, such as PP for example.

As discussed in greater detail below, the rear surface 402 of the curved support plate 400 forms a portion of the lamp support surface 1001. In the illustrated embodiment, the rear surface 402 of the curved support plate 400 and the rear surface 512 of the anchor component 500 collectively define the lamp support surface 1001 to which the each of the first and second lamps 300A-B is mounted. It should be noted that in certain embodiments, either the anchor component 500 or the curved support plate 400 can be omitted such that the lamp support structure 1000 is formed only by the other one of the anchor component 500 or the curved support plate 400. In still other, embodiments, the lamp support structure 1001 can simply be a component having a curved lamp support surface.

The rear surface 402 of the curved support plate 400 has a concave curvature which, in certain embodiments, generally corresponds to the arch of a user's denture. The front surface 401 of the curved support plate 400, on the other hand, has a convex curvature. In one embodiment, the concave curvature of the rear surface 402 matches the convex curvature of the front surface 401 so that the curved support plate has a generally constant thickness along its length.

The curved support plate 400 comprises a central aperture 403 extending therethrough. The central aperture 403 is provided to allow the anchor portion 520 of the anchor component 500 to protrude from the front surface 401 of the curved support plate 400 when the curved support plate 400 and the anchor component 500 are coupled together. The front surface 402 of the curved support plate 400 further comprises a plurality of depressions 404A-D formed therein. Each of the depressions 404A-D comprises a floor 405A-D and a basin wall 406A-D. A channel 407A-D is provided in each of the basin walls 406A-D respectively that forms a passageway between the depressions 404A-D and the central aperture 403. As discussed below, the channels 407A-D allow for the flow of melted thermoplastic elastomer during the injection overmolding of the guard component 700 to flow into the depressions 404A-D, thereby forming elastomeric pad portions 770A-D in the depressions 404A-D.

The curved support plate 400 further comprises a lamp registration feature that maintains the flexible lamps 300A-B in their selected positions relative to the curved support plate 400. As illustrated, the lamp registration feature comprises first and second ribs 421A-B that protrude from the rear surface 402 of the curved support plate 400. As can be seen, each of the first and second ribs 421A-B comprises two U-shaped rib sections that are designed to engage the corners of the first and second flexible lamps 300A-B. While the lamp registration feature is illustrated as two ribs, the lamp registration feature can take on a wide variety of structures, such as, without limitation, posts, notches, tabs, overhangs, and combinations thereof The curved support plate 400 also comprises a plurality of apertures 422A-D that are provided to mate with the plurality of protuberances 540A-D of the anchor component 500 when the curved support plate 400 and the anchor component 500 are coupled together. The apertures 422A-D are located on tabs 423-D that extend into the central aperture 403. In other embodiments, the apertures 422A-D may be located elsewhere on the curved support plate 400.

Figure 17:
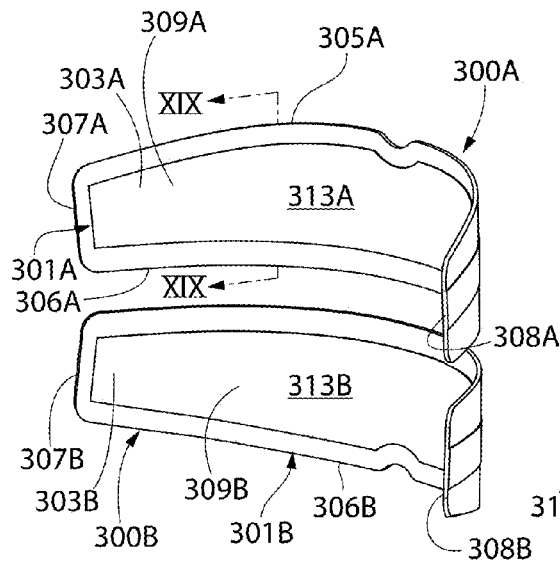
FIG. 17 is a rear perspective view of the first and second flexible lamps of the teeth whitening device of FIG. 1.
Figure 18:
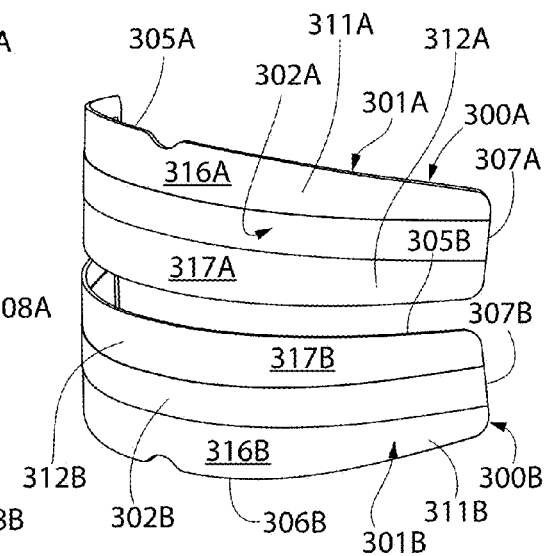
FIG. 18 is a front perspective view of the first and second flexible lamps of the teeth whitening device of FIG. 1.
Figure 19:
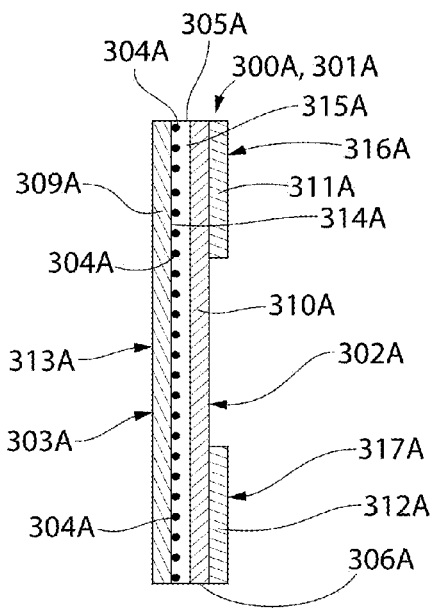
FIG. 19 is a cross-sectional view of the first and second flexible lamps of the teeth whitening device of FIG. 1 taken along view XIX.

Referring now to FIGS. 17-19 concurrently, first and second lamps 300A-B according to the present invention are illustrated. While only the cross-section of the first lamp 30A is shown in FIG. 19, it is to be understood that the second lamp 300b has the same laminate structure as that of the first lamp 300A.

Each of the first and second lamps 300A-B comprise a flexible sheet body 301A-B respectively. As illustrated, the flexible sheet body 301A-B of each of the first and second lamps 300A-B is an elongated sheet that is sufficiently flexible such that it can be bent from a planar state into a contoured shape having a curvature that generally corresponds to the arch of a user's dentiture. In one embodiment, the flexible sheet body 301A-B of each of the first and second lamps 300A-B is in a planar state when no bending force is applied to the lamp 300A-B.

The flexible sheet body 301A-B of each of the first and second lamps 300A-B generally comprises a front surface 302A-B and a rear surface 303A-B. Each of the first and second lamps 300A-B also comprises a plurality of light emitters 304A-B embedded within the flexible sheet body 301A-B that generate light which is emitted from the rear surface 303A-B of the flexible sheet body 301A-B (see FIGS. 34-35 also). In on embodiment, the light emitted by the plurality of light emitters 304A-B has a wavelength in a range of 375 nm to 520 nm. In another embodiment, the light emitted by the plurality of light emitters 304A-B has a wavelength in a range of 400 nm to 430 nm. In a further embodiment, the light emitted by the plurality of light emitters 304A-B has a wavelength in a range of 405 nm to 415 nm.

The flexible sheet body 301A-B of each of the first and second lamps 300A-B comprises an upper edge 305A-B, a lower edge 306A-B, a first side edge 307A-B, and a second side edge 308A-B. The flexible sheet body 301A-B of each of the first and second lamps 300A-B also comprises a length measured from the first side edge 307A-B to the second side edge 308A-B. The flexible sheet body 301A-B of each of the first and second lamps 300A-B is a laminate structure that generally comprises a flexible lens plate 309A-B, a flexible reflective layer 310A-B, and first and second electrical contacts 311A-B, 312A-B. The plurality of light emitters 304A-B are disposed between the flexible lens plate 309A-B and the flexible reflective layer 310A-B. As mentioned below, the plurality of light emitters 340A-B may be printed directly to the flexible lens plate 309A-B in certain embodiments. Moreover, in certain embodiments, the flexible reflective layer 310A-B may also be printed onto the flexible lens plate 309A-B subsequent to the plurality of light emitters 340A-B.

In one embodiment, the flexible lens plate 309A-B of the flexible sheet body 301A-B of each of the first and second lamps 300A-B has a rear surface 313A-B and a front surface 314A-B. The rear surface 313A-B of the flexible lens plate 309A-B forms the rear surface 303A-B of the flexible sheet body 301A-B of each of the first and second lamps 300A-B. The flexible lens plate 309A-B may be formed of a transparent biocompatible material, such as transparent PET. The plurality of light emitters 304A-B, in one embodiment, are light emitting diodes ("LEDs") printed to the front surface 314A-B of the flexible lens plate 309A-B of the flexible sheet body 301A-B of each of the first and second lamps 300A-B. In one such embodiment, the LEDs may be printed to the front surface 314A-B with an electrically conductive ink 315A-B.

Printed LEDs may be formed by depositing micro LED chips via a conductive ink formulation that can be printed in any shape to best conform to the teeth and jaw structure, which is ideal for optimized efficacy. Specifically, gallium nitride may be used to form the LEDs in some embodiments, which may then be mixed with resin and binders to form an ink, and a standard screen printer may be used to deposit the resulting ink over a desired surface. Although described herein as being printed LEDs, the plurality of light emitters 304A-B may, in certain embodiments, be any type of light source, particularly solid state light sources, which may include LEDs, OLEDs, HBLEDs, electroluminescent elements, or the like. In certain other embodiments, the plurality of light emitters 304A-B can be printed inorganic LEDs, micro conventional LEDs that are surface mounted to a flexible substrate/circuit, organic LEDs (OLEDs), or electroluminescence. In still other embodiments, the plurality of light emitters 304A-B can be any of the LEDs noted herein mounted to a rigid rather than a flexible substrate.

For each of the first and second lamps 300A-B, the first electrical contact 311A-B has a first contact surface 316A-B that forms a first portion of the front surface 302A-B of the flexible sheet body 301A-B. Similarly, for each of the first and second lamps 300A-B, the second electrical contact 312A-B has a second contact surface 317A-B that forms a second portion of the front surface 302A-B of the flexible sheet body 301A-B.

As illustrated, for each of the first and second lamps 300A-B, each of the first and second electrical contacts 311A-B, 312A-B is in the form of an elongated strip that extends the entire length of the lamp 300A-B. For the first lamp 300A (which is the upper lamp in the mouthpiece 101), the first electrical contact 311A is adjacent the upper edge 305A while the second electrical contact 312A is adjacent the lower edge 306A. For the second lamp 300B (which is the lower lamp in the mouthpiece 101), the first electrical contact 311B is adjacent the lower edge 306B while the second electrical contact 312B is adjacent the upper edge 305B. For each of the first and second lamps 300A-B, the first electrical contact 311A-B extends generally parallel to and second electrical contact 312A-B.

In one embodiment, each of the first and second lamps 300A, 300B has an illumination area (i.e., area of the rear surface 303A-B that comprises plurality of light emitters 304A-B) that is in a range of 6 $cm^2$ to 11 $cm^2$, more preferably in a range of 7 $cm^2$ to 10 $cm^2$, and most preferably in a range of 8 $cm^2$ to 9 $cm^2$. The height of illumination area may be in a range of 0.5 $cm^2$ to 3 $cm^2$, and more preferably 0.5 $cm^2$ to 2 $cm^2$, with 1 $cm^2$ being most preferred. The length of illumination area may be in a range of 6 cm to 11 cm, more preferably in a range of 7 cm to 10 cm, and most preferably in a range of 8 cm to 9 cm.

Figure 20:
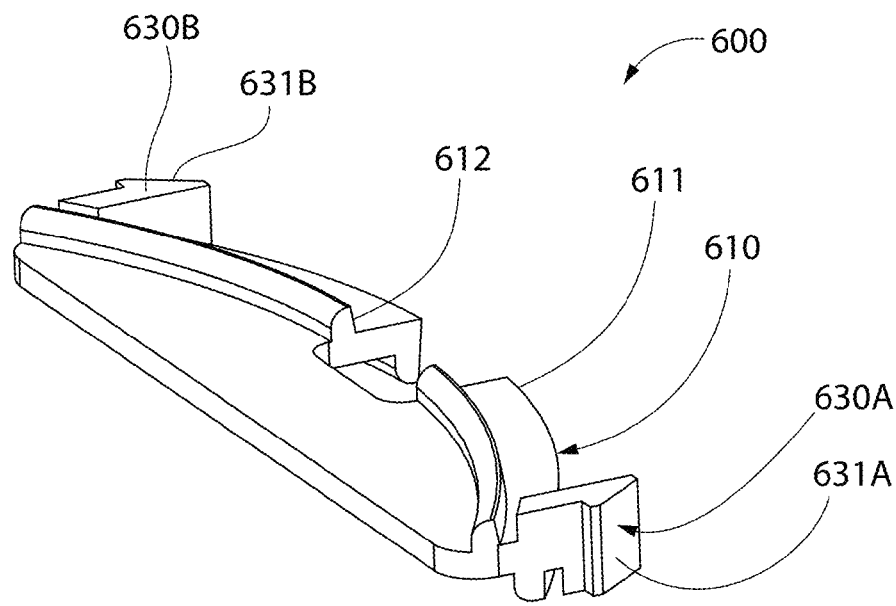
FIG. 20 is a rear perspective view of the lamp retaining component of the teeth whitening device of FIG. 1.
Figure 21:
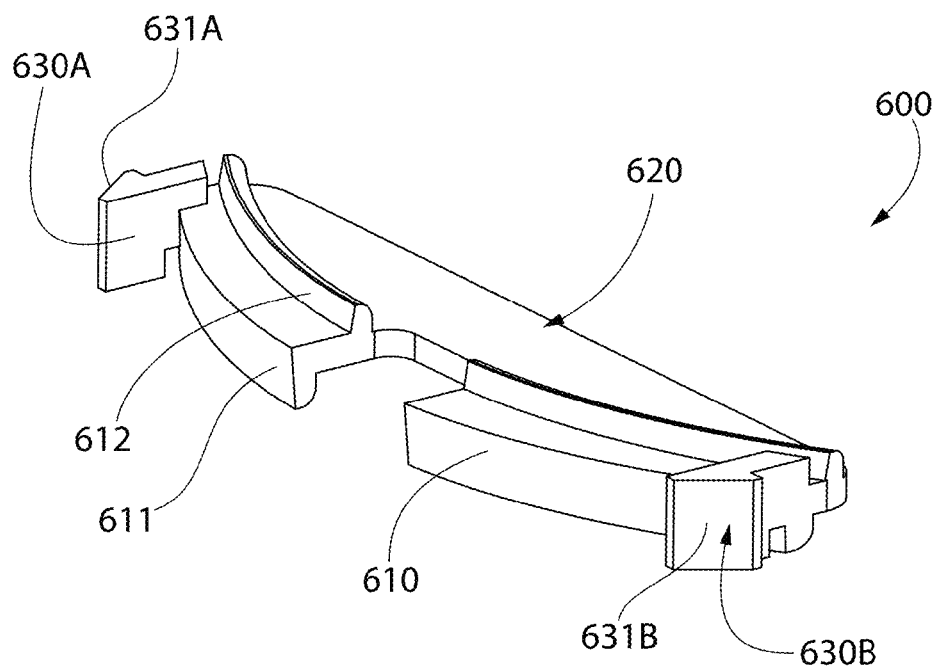
FIG. 21 is a front perspective view of the lamp retaining component of the teeth whitening device of FIG. 1.

Referring now to FIGS. 20-21 concurrently, a lamp retaining component 600 is illustrated according to an embodiment of the present invention. As will be discussed in greater detail below, the lamp retaining component 600 is used to retain the first and second lamps 300A-300B to the lamp support surface 1001 when the mouthpiece is assembled (and during the injection molding of the guard component 700 to the lamp assembly 2000). The lamp retaining component 600, in one embodiment, is formed of a rigid material, such as a hard plastic. Suitable hard plastics include without limitation polymers and copolymers of ethylene (polyethylene), propylene (polypropylene), butadiene, polyamide, cellulosic, SAN, acrylic, ABS, vinyl compounds, and polyesters such as polyethylene terephthalate, or other commonly known thermoplastics used in oral hygiene device manufacture.

The lamp retaining component 600 generally comprises a lamp engagement portion 610 and a plate portion 620. The lamp engagement portion 610 comprises a first arched surface 611 that contacts the lower portion of the first lamp 300A and a second arched surface 612 that contacts the upper portion of the second lamp 300B. As can be seen, because the lamps 300A-B, in one embodiment, are supported on the lamp support surface 1001 in a horizontally offset manner, the first and second arched surfaces 611, 612 of the lamp retaining component 600 are also horizontally offset from one another in certain embodiments.

The lamp retaining component 600 further comprises a locking feature that locks the lamp retaining component 600 to the anchor component 500 to ensure that the lamps 300A-B are compressed therebetween and/or held in place. In the illustrated embodiment, the locking feature of the lamp retaining component 600 comprises first and second locking tabs 630A-B, which are configured to snap-lock to the anchor component 500. More specifically, the lamp retaining component 600 is coupled to the anchor component by inserting the first and second locking tabs 630A-B through the locking apertures 531A-B of the anchor component 500. During insertion, the chamfered surfaces 631A-B of the first and second locking tabs 630A-B contact the rear surface 512 of the curved plate section 510 of the anchor component 500 and deflect the first and second locking tabs 630A-B. Once fully inserted through the locking apertures 531A-B of the anchor component 500, the first and second locking tabs 630A-B snap back into their normal state, thereby causing locking surfaces 632A-B of the first and second locking tabs 630A-B to mate with and mechanically engage an edge portion of the curved plate section 510 of the anchor component 500 that defines the locking apertures 531A-B of the anchor component 500.

As can be seen, the plate portion 620 is a flat plate structure that extends horizontally from the lamp engagement section 610. When the mouthpiece 101 is assembled, the plate portion 620 of the lamp retaining component 600 extends horizontally from the lamp support surface 1001 (see FIG. 30). As will be described in further detail below, the lamp retaining component 600 is embedded in the bite platform of the mouthpiece 101 when the mouthpiece is fully assembled in certain embodiments. In addition to retaining the first and second lamps 300A-300B to the lamp support surface 1001, the lamp retaining component 600 also assists with maintaining the proper contour of the arch-shaped wall 104 of the mouthpiece 101.

In certain embodiments, the lamp retaining component 600 may be omitted all together. In such an embodiment, the function of the lamp retaining component 600 may be performed by the guard component. In other embodiments, the lamp retaining component 600 may be integrated into the lamp support structure. In another embodiment, the lamp support structure may include a plat portion, similar to plat portion 620 that protrudes from the lamp support surface.

Figure 22:
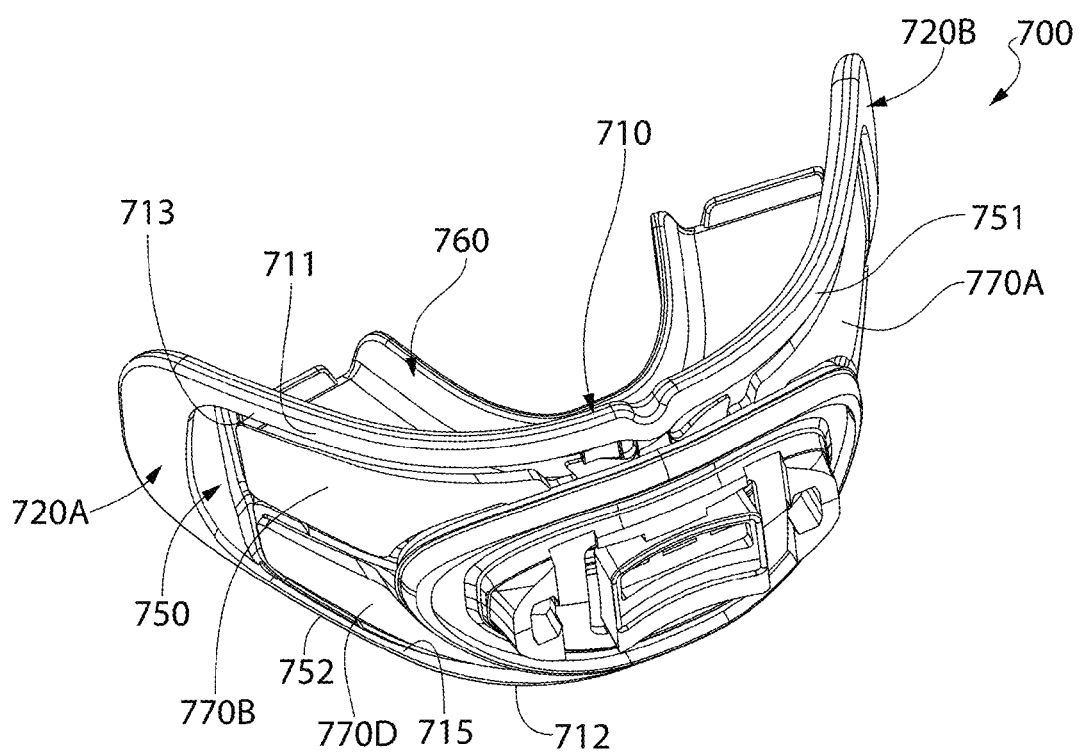
FIG. 22 is a front perspective view of the guard component of the teeth whitening device of FIG. 1.
Figure 23:
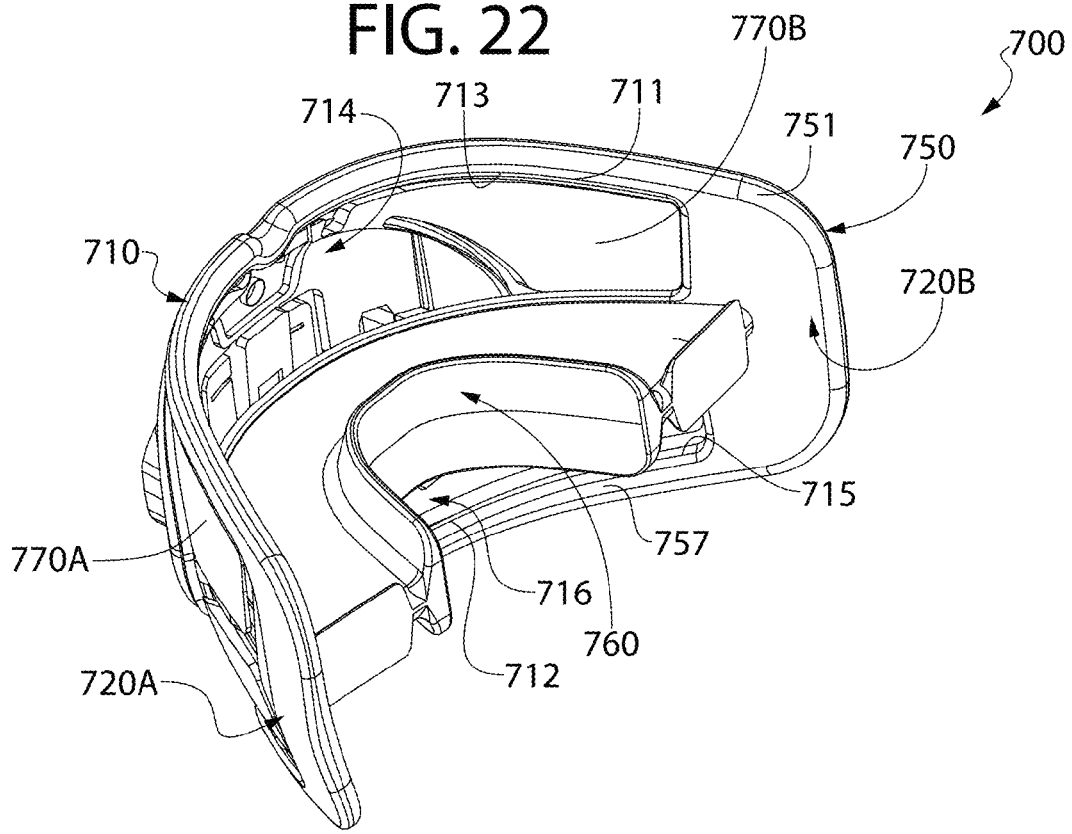
FIG. 23 is a rear perspective view of the guard component of the teeth whitening device of FIG. 1.

Referring now to FIGS. 22-24 concurrently, a guard component 700 according to the present invention is illustrated. The guard component 700, in the illustrated embodiment, is an integrally formed monolithic component. In one embodiment, the guard component 700 is formed of a material so as to provide comfort to the user when the mouthpiece 101 is inserted into the oral cavity. In one such embodiment, the material of which the guard component 700 is formed has a hardness value that is less than the hardness value of the material (or materials) of which the lamp support structure 1000 is formed (in the illustrated embodiment the lamp support structure 1000 is formed by the combination of the anchor component 500 and the curved support plate 400, but may be a singular component in other embodiments). To this end, in one embodiment, the guard component 700 is formed of an elastomeric material. Suitable elastomeric materials include, without limitation, thermoplastic elastomers, rubbers, silicones, or other biocompatible resilient materials suitable for uses in an oral hygiene apparatus including thermoset elastomers or the like.

The guard component 700 generally comprises a wall portion 750 and a bite platform portion 760. The bite platform portion 760 extends horizontally from the wall portion 750. The wall portion 750 can conceptually be divided into an upper wall portion 751 and a lower wall portion 752. In embodiments that include the bite platform portion 760, the bite platform portion 760 is located between the upper and lower wall portions 751-752. In other embodiments, the bite platform portion 760 may be omitted.

The wall portion 750 comprises a central portion 710 and first and second wing portions 720A-B. The central portion 710 is arcuate in shape and has a curvature that corresponds to the anterior portion of the arch of the human dentiture. The first and second wing portions 720A-B extend from and are located on opposite sides of the central portion 710, thereby generally continuing the curvature that corresponds to the arch of the human dentiture. As will be discussed in greater detail below, the first and second wing portions 720A-B, in certain embodiments, are formed entirely out of the elastomeric material in order to ensure flexibility for user comfort. In certain such embodiments, the first and second wing portions 720A-B retain their flexible nature as the lamp support structure 1000 does not extend into the first and second wing portions 720A-B but rather are only located in the central portion 710.

The central portion 710 comprises a first frame portion 711 and a second frame portion 712. More specifically, the upper wall portion 751 comprises the first frame portion 711 while the lower wall portion 752 comprises the second frame portion 712. The first frame portion 711 comprises a closed-geometry edge 713 that defines a first window 714 through which the rear surface 303A of the first lamp 300A remains exposed when the mouthpiece 101 is assembled. The second frame portion 712 comprises a closed-geometry edge 715 that defines a second window 716 through which the rear surface 303B of the second lamp 300B remains exposed when the mouthpiece 101 is assembled. As will be discussed in greater detail below, when the mouthpiece 101 is assembled, the first frame portion 711 seals a perimeter of the rear surface 303A of the first lamp 300A while the second frame portion 712 seals a perimeter of the rear surface 303B of the second lamp 300B.

The guard component 700 further comprises a plurality of pad portions 770A-D. When the mouthpiece is assembled, the plurality of pad portions 770A-D are respectively disposed in the plurality of depressions 404A-D of the curved support plate 400. Allowing molten elastomeric material to flow into the depressions to form the plurality of pad portions 770A-D assists in equalizing pressure on the first and second lamps 300A-B during the injection molding process in which the guard component 700 is overmolded to the lamp support structure 1000. In the illustrated embodiment, first and second pad portions 770A-B are located within the first window 714 while the third and fourth pad portions 770C-D are located within the second window 716. The first and second pad portions 770A-B are located within the first and second depressions 404A-B respectively and contact both the floors 405A-B of the first and second depressions 404A-B and the front surface 312A of the first lamp 300A. The third and fourth pad portions 770C-D are located within the third and fourth depressions 404C-D respectively and contact both the floors 405C-D of the third and fourth depressions 404C-D and the front surface 312B of the second lamp 300B.

Referring now to FIGS. 25-34, the assembly of the teeth whitening device 100, along with a discussion of the teeth whitening device 100 in the assembled state will be set forth. Beginning with FIG. 28, the curved support plate 400 is provided. The curved support plate 400, in one embodiment, is formed out of a first material, such as a hard plastic, using an injection molding or other suitable process. Suitable hard plastics include without limitation polymers and copolymers of ethylene (polyethylene), propylene (polypropylene), butadiene, polyamide, cellulosic, SAN, acrylic, ABS, vinyl compounds, and polyesters such as polyethylene terephthalate, polycarbonate (or blends thereof) or other commonly known thermoplastics used in oral hygiene device manufacture. In other embodiments, the first material may be another suitable rigid material that can properly support and protect the flexible lamps 300A-B during the injection molding process of the guard component 700 (discussed below).

Figure 29:
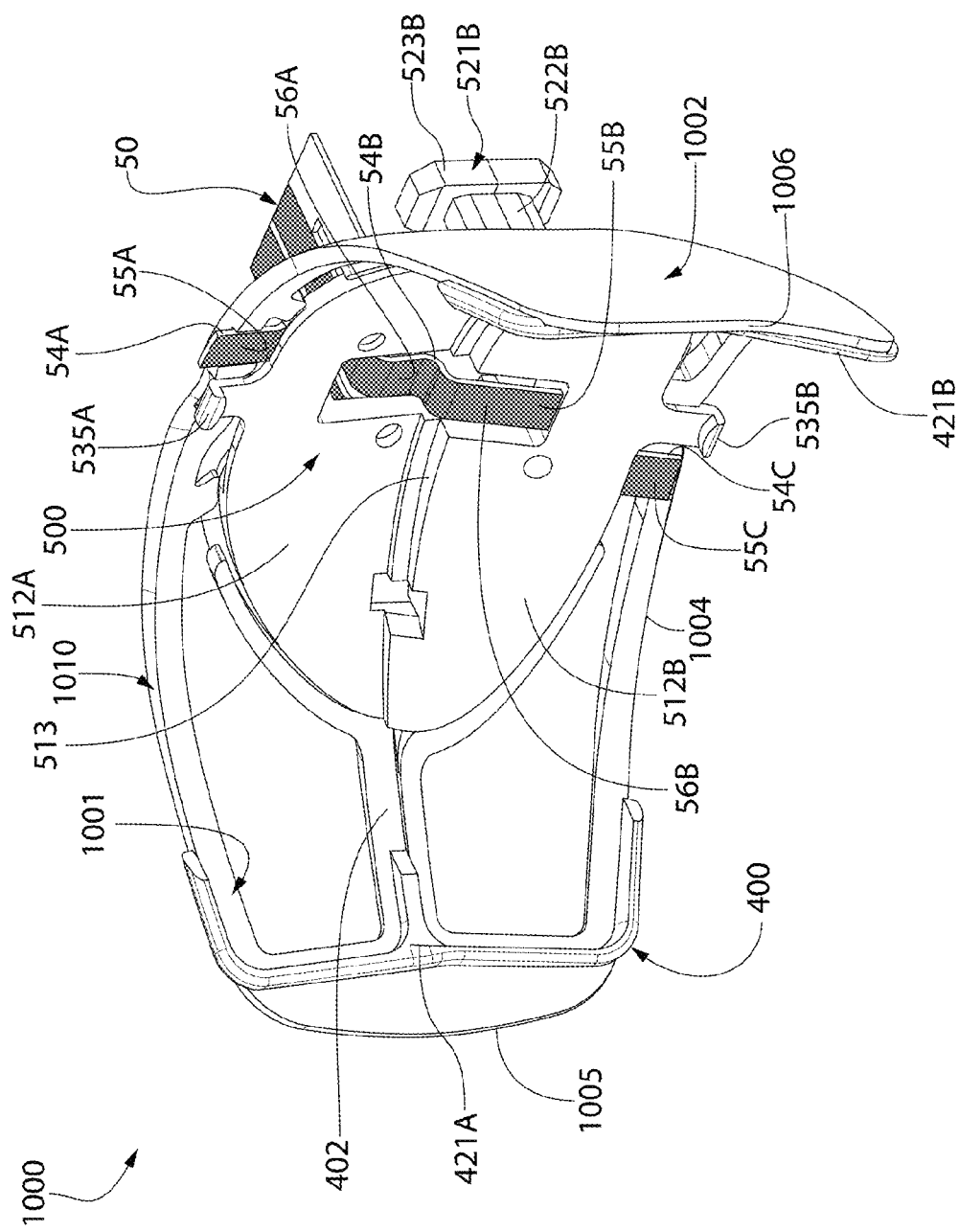
FIG. 29 is a rear perspective of the curved support plate of FIG. 28 with the anchor component coupled thereto to form a lamp support structure in accordance with an embodiment of the invention.

Referring now to FIGS. 25 and 29, the anchor component 500 is provided and coupled to the curved support plate 400, thereby forming a lamp support structure 1000. Because the lamp support structure 1000 is formed by the combination of the anchor component 500 and the curved support plate 400, it should be noted that for purposes of this patent, it can be said that the lamp support structure 1000 comprises the various features of either of these components as described above for FIGS. 12-13 and 14-16.

In coupling the anchor component 500 to the curved support plate 400, the anchor section 510 of the anchor component 500 is inserted through the central aperture 403 of the curved support plate 400. As the anchor section 510 passes through the central aperture 403, the plurality of protuberances 540A-D protruding from the front surface 511 of the anchor component 500 respectively enter the plurality of apertures 422A-D of the curved support plate 400, thereby ensuring proper relative alignment and mating between the anchor component 500 and the curved support plate 400. In the illustrated embodiment, the electrical contact component 50 has been previously mounted to the anchor component 500, prior to mounting to the curved support plate 400. Thus, in FIG. 29, the electrical contact component 50 is already mounted and integrated into the lamp support structure 1000.

While the lamp support structure 1000, in the illustrated embodiment, is formed by the combination of the anchor component 400 and the curved support plate 500, the lamp support structure 1000 may be an integrally-formed single component structure in other embodiments. In still other embodiments, more than two components can be used to form the lamp support structure 1000.

The lamp support structure 1000 comprises a lamp support surface 1001 (which is formed by the combination of the rear surfaces 402, 512 of the curved support plate 400 and anchor component 500 in the illustrated embodiment). The lamp support surface 1001 has a concave curvature which, in one embodiment, generally corresponds to the arch of the human dentiture. The lamp support structure 1000 further comprises a front surface 1002 (which is formed by the combination of the front surfaces 401, 511 of the curved support plate 400 and anchor component 500 in the illustrated embodiment). Thus, the lamp support structure 1000 comprises a curved plate section 1010 that has a first thickness measured from the front surface 1002 to the lamp support surface 1001. In one embodiment, each of the first and second lamps 300A-B have a second thickness measured from the rear surface 303A-B of the flexible sheet body 301A-B to the front surface 302A-B of the flexible sheet body 301A-B. In one embodiment, a ratio of the first thickness to the second thickness is in a range 0.5 to 2.5.

The lamp support structure 1000 comprises an upper curved edge 1003, a lower curved edge 1004, a first side edge 1005 extending between the upper and lower curved edges 1003, 1004, and a second side edge 1006 extending between the upper and lower curved edges. The anchor elements 521A-B protrude from the front surface 1002 of the lamp support structure 1000. The lamp support structure 1000 further comprises the lamp registration feature 421A-B, the lamp retaining feature 535A-B, and the depressions 405A-D formed in the lamp support surface 1001, as described in greater detail above with respect to FIGS. 12-13 and 14-16.

The electrical contact component 50 is mounted to the lamp support structure 1000 so that electrical coupling of the first and second lamps 300A-B can be easily accomplished. Specifically, electrical contact component 50 is mounted to the lamp support structure 1000 so that: (1) the first contact surface 55A of the first electrical contact element 54A forms a portion of the lamp support surface 1001; (2) the second contact surface 55B of the second electrical contact element 54B forms a portion of the lamp support surface 1001; and (3) the third contact surface 55C of the third electrical contact element 54C forms a portion of the lamp support surface 1001. In one embodiment, the first, second and third contact surfaces 55A-C of the electrical contact component 50 are substantially flush with the remainder of the lamp support surface 1001. In the illustrated embodiment, each of the first, second and third contact surfaces 55A-C of the electrical contact component 50 are located in a central portion (horizontally) of the lamp support structure, wherein the second contact surface 55B of the second electrical contact element 54B is centrally located (vertically) while the first contact surface 55A of the first electrical contact element 54A is located adjacent the upper curved edge 1003 and the third contact surface 55C of the third electrical contact element 54C is located adjacent the lower curved edge 1004.

As can be seen, the lamp support structure 1000 is a stepped surface in the central region, with the tread surface portion 513 forming the step between the upper and lower surface portions 512A, 512B, which are horizontally offset from one another. Conceptually, the upper surface portion 512A can be considered a first riser portion of the lamp support surface 1001 while the lower surface portion 512B can be considered a second riser portion of the lamp support surface 1001. In the illustrated embodiment, the second contact surface 55B is also a stepped surface comprising a first portion 56A and a second portion 56B that are horizontally offset from one another. The first portion 56A of the second contact surface 55B is in surface alignment with the upper surface portion 512A while the second portion 56B of the second contact surface 55B is in surface alignment with the lower surface portion 512B.

Figure 26:
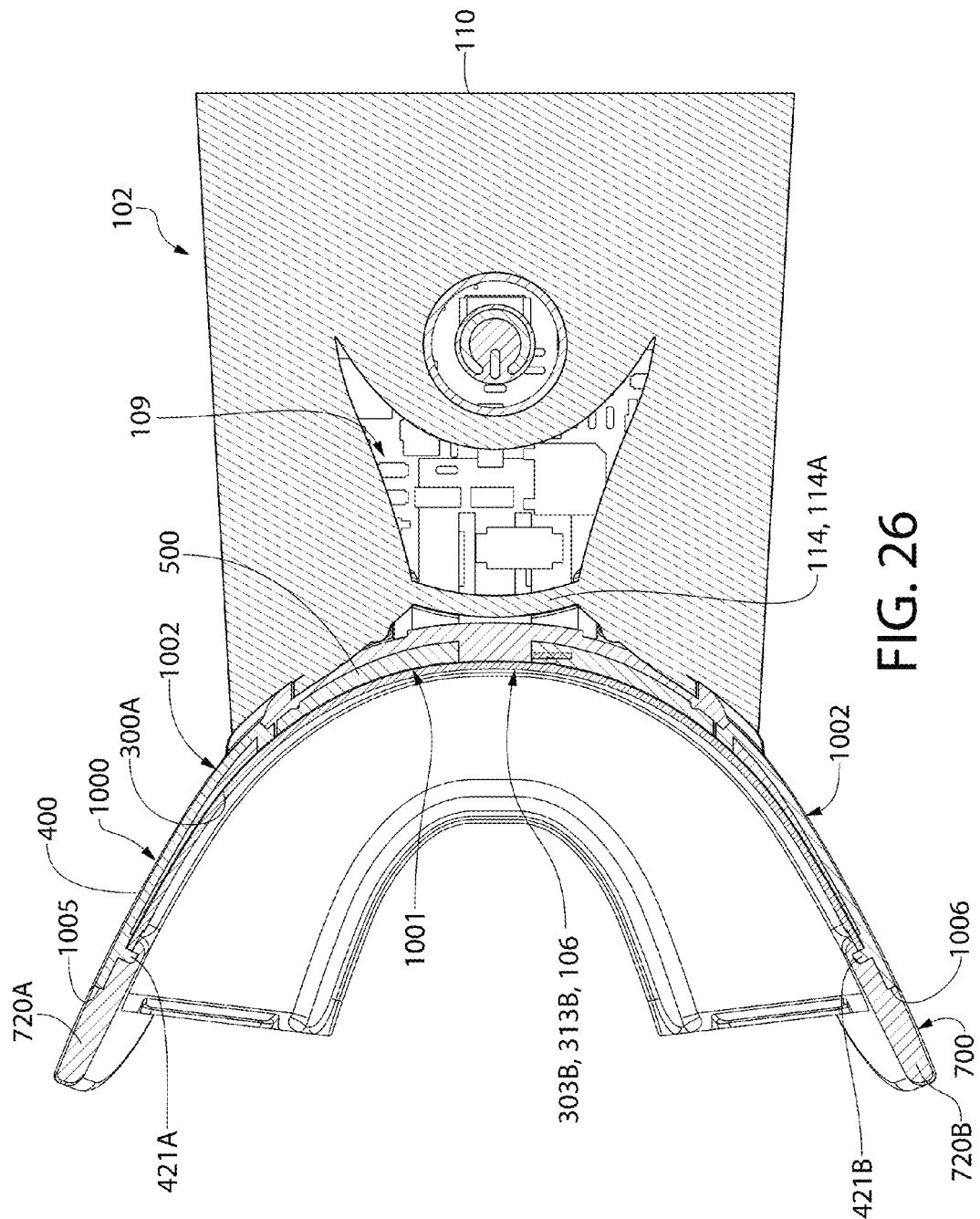
FIG. 26 is a cross-sectional view of the teeth whitening device of FIG. 1 taken along view XXV of FIG. 4.
Figure 30:
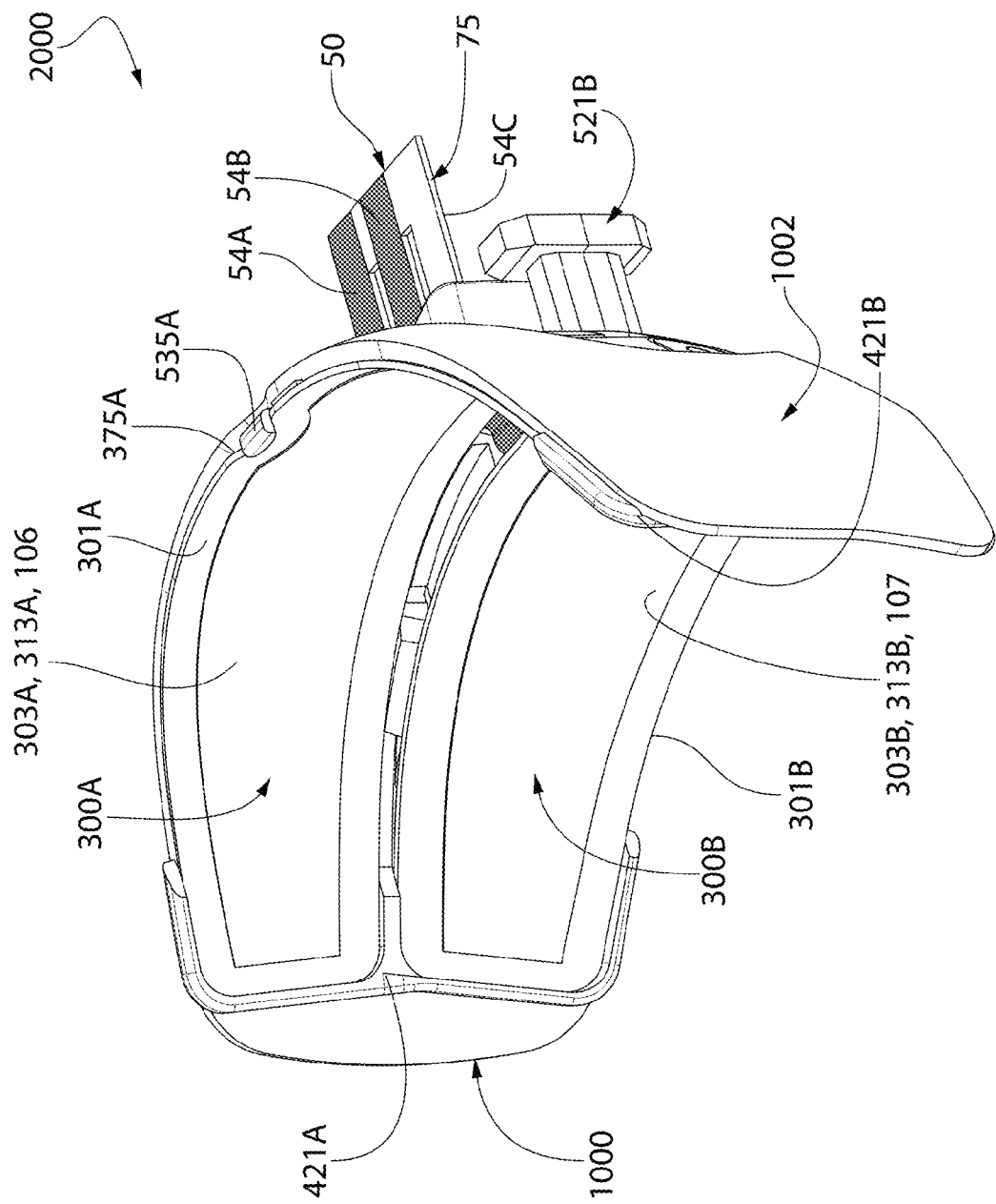
FIG. 30 is a rear perspective view of the lamp support structure of FIG. 29 with the first and second flexible lamps mounted to the lamp support surface thereof, thereby forming a lamp assembly in accordance with an embodiment of the invention.

Referring now to FIGS. 25-26 and 30 concurrently, once the lamp support structure 1000 is provided, the first and second lamps 300A-B are mounted to the lamp support surface 1001 of the lamp support structure 1000, thereby forming a lamp assembly 2000. Because the first and second lamps 300A-B are flexible, the lamps 300A-B flex to assume the curvature of the lamp mounting surface 1001, thereby resulting in the rear surfaces 313A-B of the flexible sheet bodies 301A-B of the first and second lamps 300A-B assuming a concave curvature. The first lamp 300A is mounted above the second lamp 300B.

On the front surfaces 302A-B of the flexible sheet bodies 301A-B of the lamps 300A-B, the first and second electrical contacts 311A-B, 312A-B of the lamps 300A-B come into surface contact with the contact surfaces 55A-C of the first, second, and third electrical contact elements 54A-C. Specifically, the first contact surface 55A of the first electrical contact element 54A is in surface contact with the first electrical contact 311A of the first lamp 300A. The third contact surface 55C of the third electrical contact element 54C is in surface contact with the first electrical contact 311B of the second lamp 300B. With respect to the second electrical contact element 54B, the first portion 56A of the second contact surface 55B contacts a second electrical contact 112A of the first flexible lamp 300A while the second portion 56B of the second contact surface 55B contacts a second electrical contact 112B of the second flexible lamp 300B. In one embodiment, the surface contact between the contact surfaces is sufficient to achieve the desired electrical coupling and, thus electrical coupling is achieved solely through surface contact. In another embodiment, the contact surfaces may be soldered together to increase reliability.

As can be seen in FIG. 30, the electrical contact component 50 has a portion 75 that protrudes from the front surface 1002 of the lamp support structure 1000 adjacent the anchor elements 521A-B. The portion 75 comprises an exposed portion of each of the first, second, and third electrical conductors 54A-C to facilitate coupling to the control circuit 200 (discussed below).

Proper positioning (and maintaining proper position) of the flexible lamps 300A-B to the lamp support structure 100 is achieved by the lamp registration feature 421A-B and the lamp retaining feature 535A-B. As discussed in greater detail above, the lamp registration feature comprises first and second ribs 421A-B that protrudes from the lamps support surface 1001. As can be seen, the second rib 421A engages first and second corners of the flexible sheet bodies 301A-B of each of the first and second lamps 300A-B while the second rib 421B engages third and fourth corners of the flexible sheet bodies 301A-B of each of the first and second lamps 300A-B. Moreover, the first and second lamp retaining features 535A-B also protrude from the lamp support surface, wherein the first retaining feature 535A engages the upper edge 305A of the first flexible lamp 300A while the second retaining feature 535B engages the lower edge 306B of the second flexible lamp 300B. As can also be seen, the first retaining feature 535A extends through a notch 375A formed in the upper edge 305A of the first flexible lamp 300A while the second retaining feature 535B extends through a notch 375B formed in the lower edge 306B of the second flexible lamp 300B.

Figure 27:
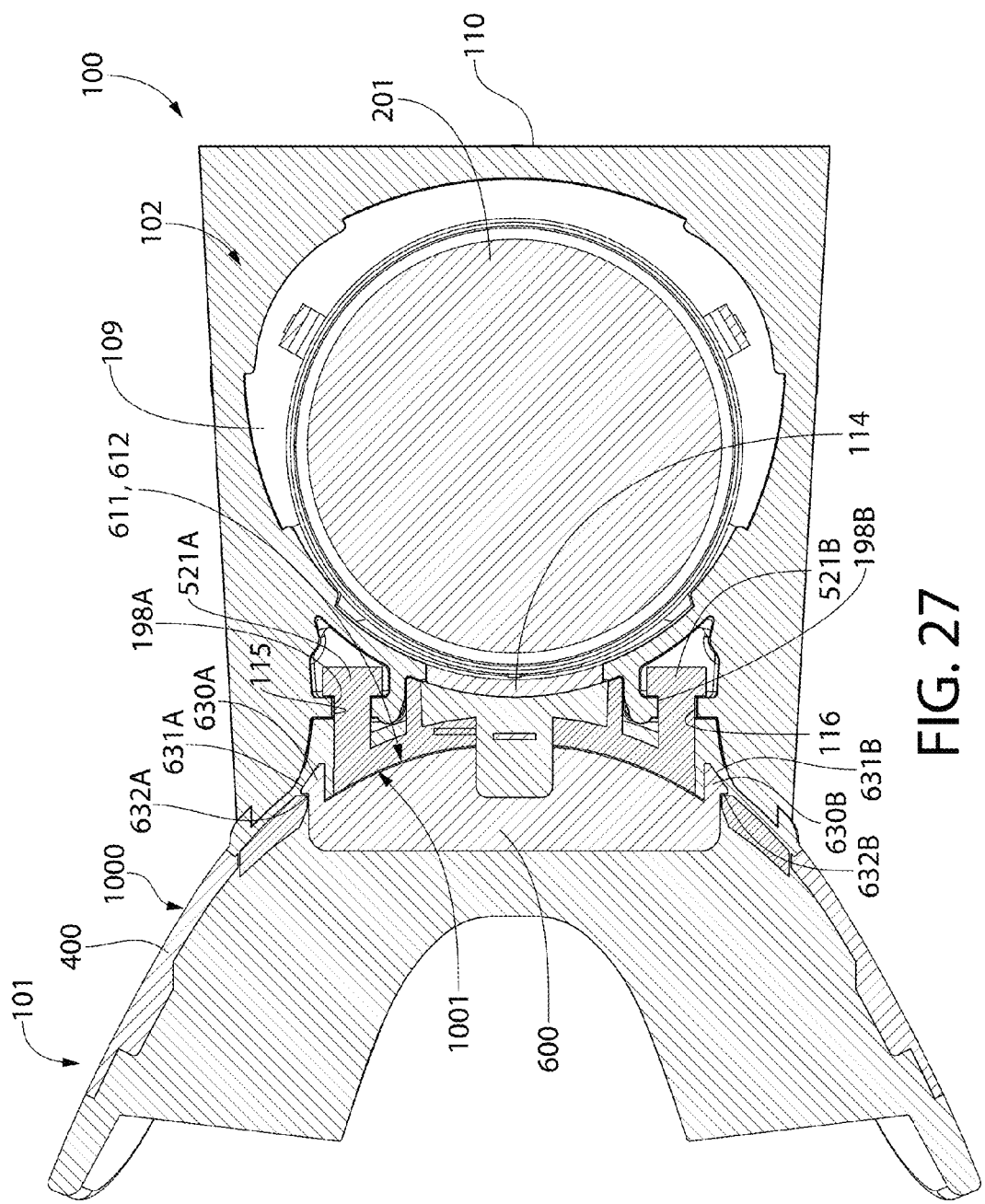
FIG. 27 is a cross-sectional view of the teeth whitening device of FIG. 1 taken along view XXVI of FIG. 4.
Figure 31:
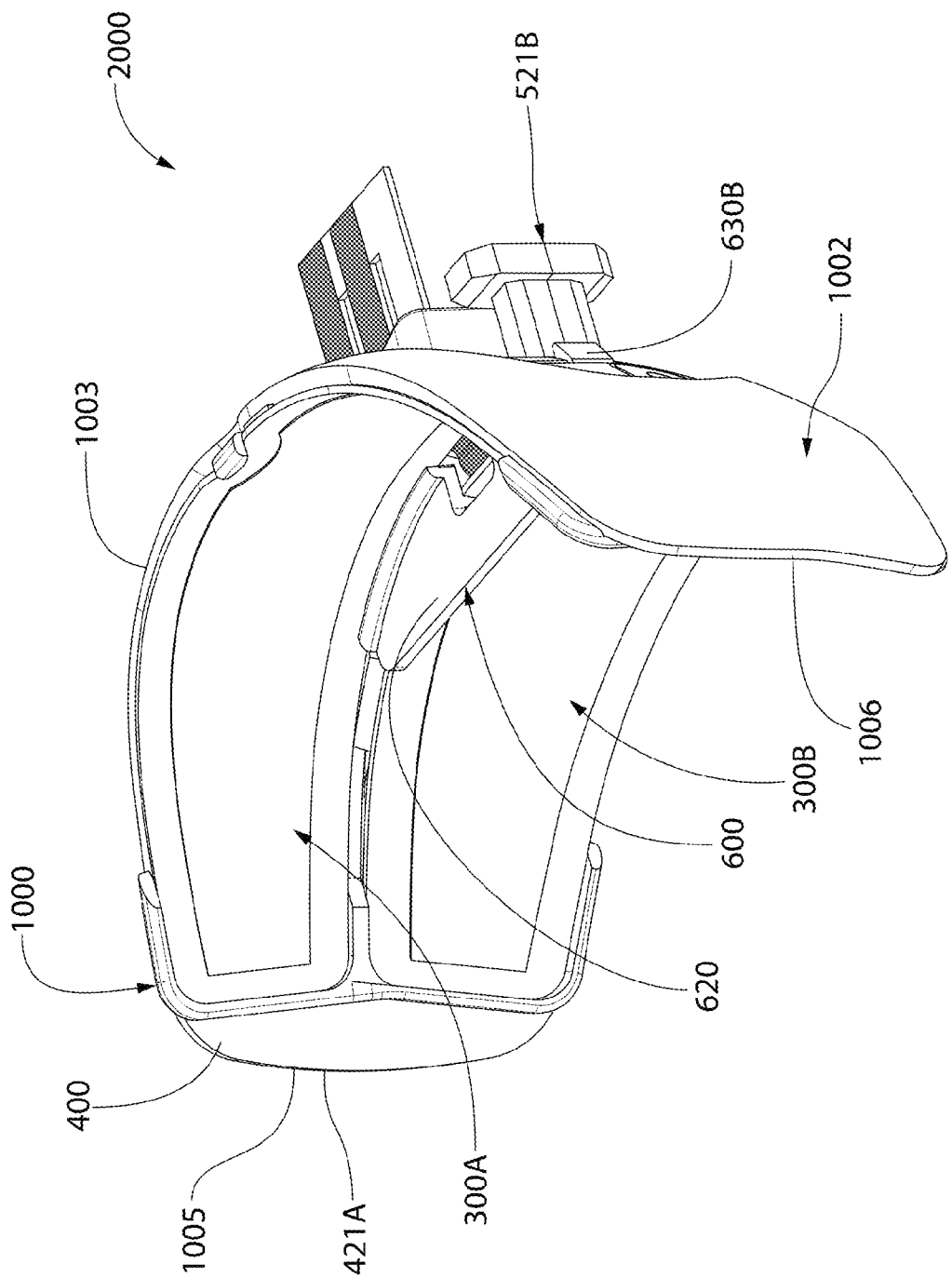
FIG. 31 is a rear perspective view of the lamp assembly of FIG. 30 with the lamp retaining component coupled thereto.
Figure 32:
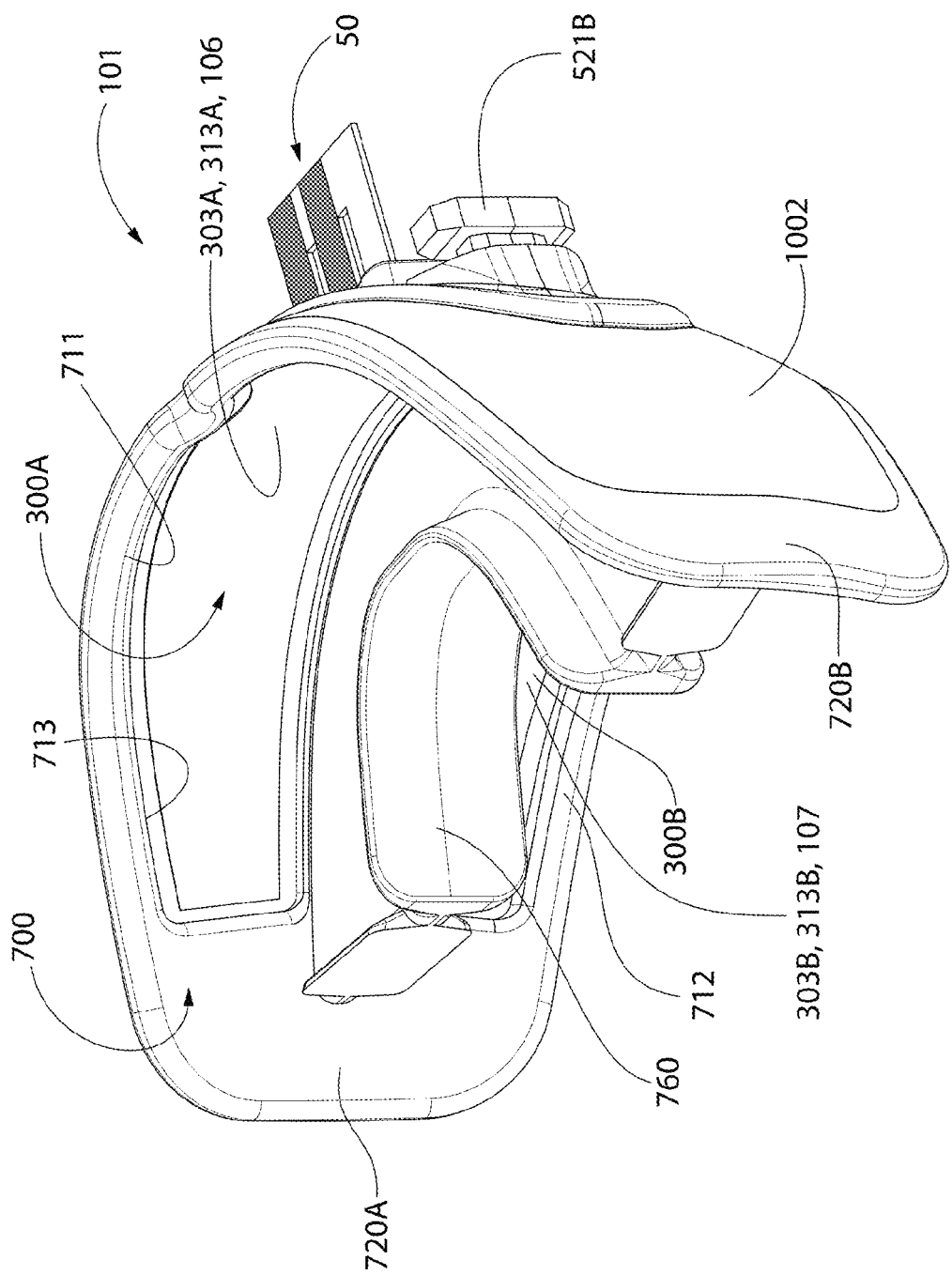
FIG. 32 is a rear perspective of the lamp assembly of FIG. 31 in which the guard component has been overmolded thereto to form the mouthpiece.

Referring now to FIGS. 25, 27 and 31 concurrently, once the first and second lamps 300A-B are in position against the lamps support surface 1001, the lamp retaining component 600 is aligned with the lamp support structure 1000 and coupled thereto. Specifically, the lamp retaining component 600 is aligned with the lamp support structure 1000 so that the first and second locking tabs 630A-B are aligned with the locking apertures 531A-B of the lamp support structure 1000. The lamp retaining component 600 is moved towards the lamp support surface 1001 so that the first and second locking tabs 630A-B are inserted through the locking apertures 531A-B of the anchor component 500. During insertion, the chamfered surfaces 631A-B of the first and second locking tabs 630A-B contact the lamp support surface 1001 and deflect the first and second locking tabs 630A-B. Once fully inserted through the locking apertures 531A-B, the first and second locking tabs 630A-B snap back into their normal state, thereby causing locking surfaces 632A-B of the first and second locking tabs 630A-B to mate with and mechanically engage the front surface 1002 of the lamp support structure 1000.

During this process, the first arched surface 611 of the lamp retaining component 600 contacts the lower portion of the first lamp 300A while the second arched surface 612 of the lamp retaining component 600 contacts the upper portion of the second lamp 300B. As a result the lamps 300A-B are pressed against the lamp support surface 1001. In one embodiment, the lower portion of the first lamp 300A may be compressed between the lamp retaining component 600 and the lamp support surface 1001 while the upper portion of the second lamp 300B is compressed between the lamp retaining component 600 and the lamp support surface 1001.

Referring now to FIGS. 25-27 and 32 concurrently, once the lamp assembly 2000 is fully assembled (as shown in FIG. 31), the guard component 700 is overmolded to the lamp assembly 2000, thereby forming the mouthpiece 101. As discussed above, the guard component 700 comprises the first and second frame portions 711, 712. The first frame portion 711 comprises the closed-geometry edge 713 that defines the first window 714 through which the rear surface 303A of the first lamp 300A remains exposed. Thus, in this embodiment, the rear surface 303A of the first lamp 300A (which is also the rear surface 313A of the flexible lens plate 309A) also acts as the first light emitting surface 106. Similarly, the second frame portion 712 comprises the closed-geometry edge 715 that defines the second window 716 through which the rear surface 303B of the second lamp 300B remains exposed when the mouthpiece 101 is assembled. Thus, in this embodiment, the rear surface 303B of the second lamp 300B (which is also the rear surface 313B of the flexible lens plate 309B) also acts as the second light emitting surface 107.

The first frame portion 711 forms an annular seal about the perimeter of the rear surface 303A of the first lamp 300A. The second frame portion 712 forms an annular seal about the perimeter of the rear surface 303B of the second lamp 300B. Additionally, during the overmolding process that forms the guard component 700, molten elastomeric material flows into the depressions 405A-D of the lamps support surface 1001, thereby forming the pad portions 770A-D. Allowing molten elastomeric material to flow into the depressions 405A-D to form the plurality of pad portions 770A-D assists in equalizing pressure on the first and second lamps 300A-B during the injection molding process in which the guard component 700 is overmolded to the lamp support structure 1000. The first and second pad portions 770A-B are located within the first and second depressions 404A-B respectively and contact both the floors 405A-B of the first and second depressions 404A-B and the front surface 312A of the first lamp 300A. The third and fourth pad portions 770C-D are located within the third and fourth depressions 404C-D respectively and contact both the floors 405C-D of the third and fourth depressions 404C-D and the front surface 312B of the second lamp 300B.

As can best be seen in FIG. 26, the guard component 700 further comprises the first wing portion 720A that extends beyond the first side edge 1005 of the lamp support structure 100 and the second wing portion 720B that extends beyond the second side edge 1006 of the lamp support structure 1000. The first and second wing portions 720A-B, in the illustrated embodiment, are formed entirely out of the elastomeric material, thereby providing flexibility at the end portions of the mouthpiece 101 for user comfort. The lamp support structure 1000 does not extend into the first and second wing portions 720A-B. However, as can be seen, once the guard component 700 is formed, at least a portion of the front surface 1002 of the lamp support structure 1000 remains exposed.

Figure 33:
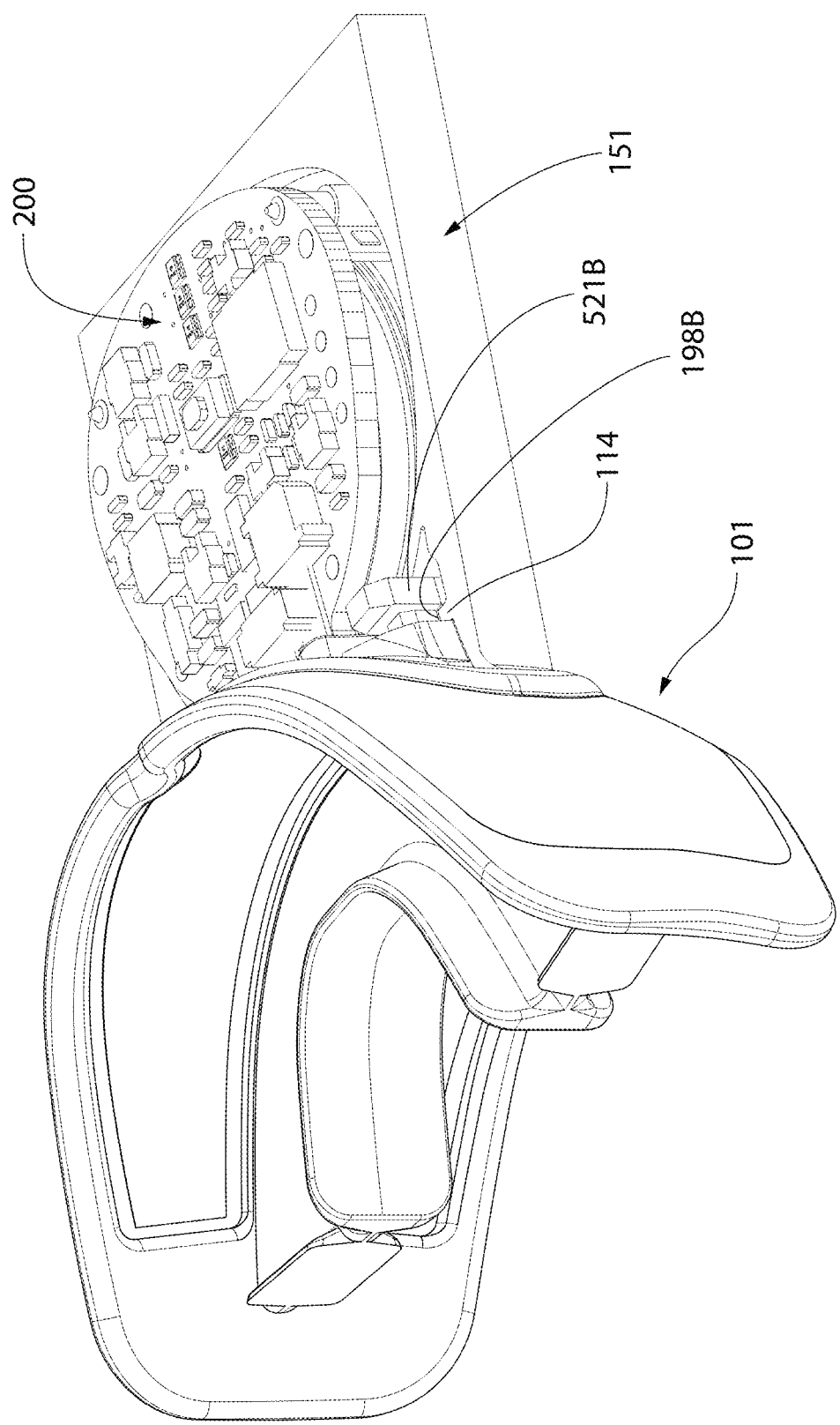
FIG. 33 is a rear perspective view of the mouthpiece of FIG. 32 positioned such that the anchor elements are in mating cooperation with the lower portion of the housing.
Figure 34:
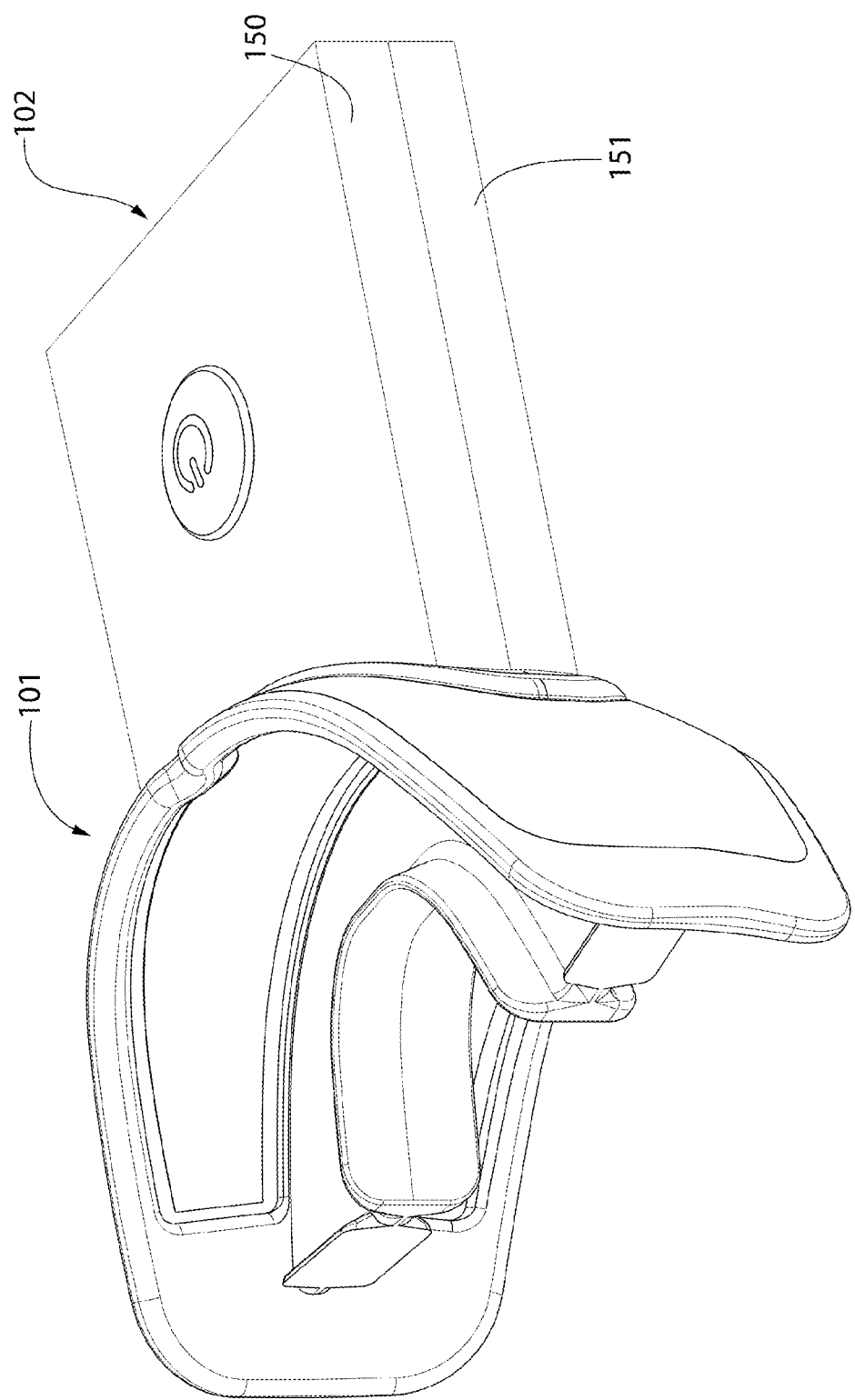
FIG. 34 is a rear perspective view of the mouthpiece of FIG. 32 in which the upper portion of the housing has been added, thereby completing assembly of the teeth whitening device of FIG. 1.
Figure 35:
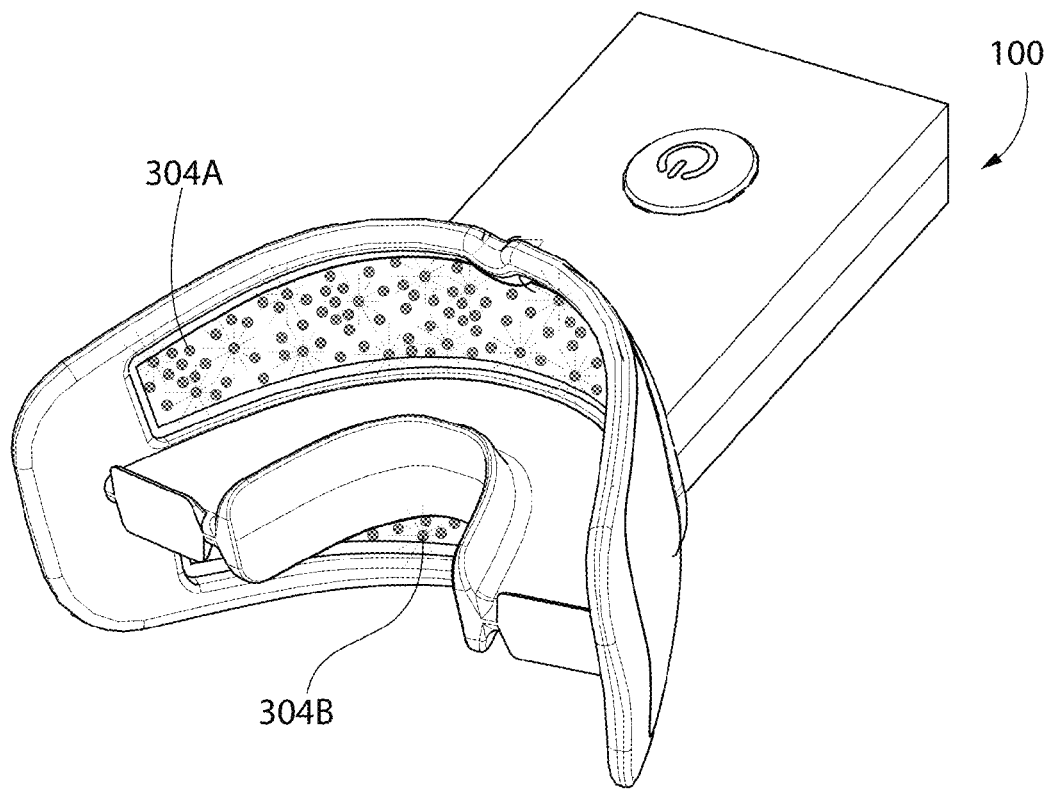
FIG. 35 is a rear perspective view of the teeth whitening device of FIG. 1 wherein the light emitters are activated and generating light.
Figure 36:
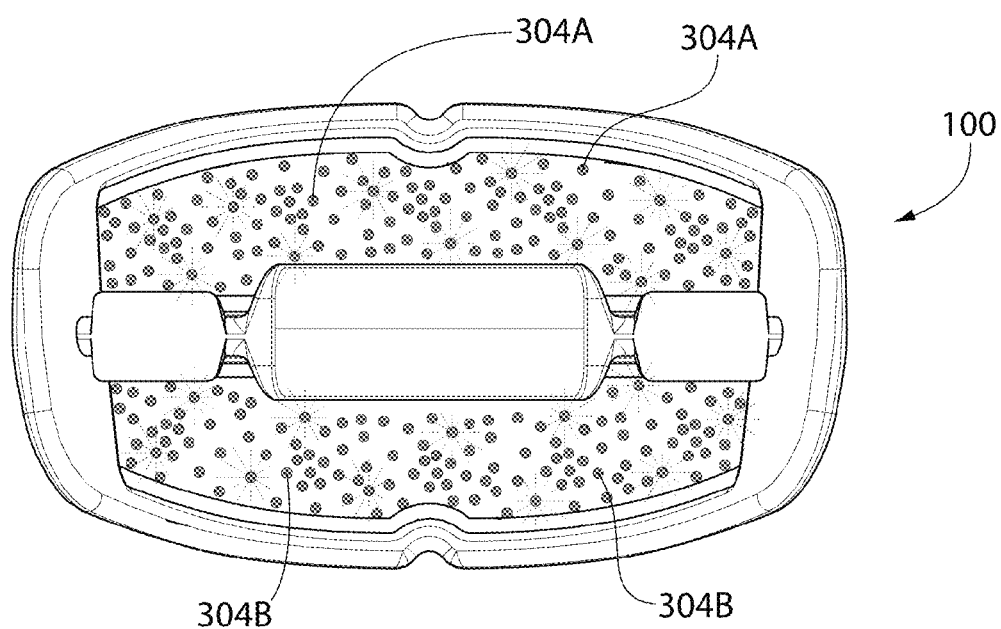
FIG. 36 is a rear view of the teeth whitening device of FIG. 35.

Referring now to FIGS. 27 and 33-34 concurrently, once the mouthpiece 101 is formed, it is coupled to the housing 102, thereby fixing the mouthpiece 101 to the housing 102 and sealing all electrical components. Specifically, the lower portion 151 of the housing 102 is provided with the control circuit 200 in position. The mouthpiece 101 is positioned so that the anchor elements 521A, 521B are above first and second open slots 198A-B formed into a lower section of the housing wall 114. The mouthpiece 101 is lowered so that the anchor elements 521A, 521B enter into the first and second open slots 198A-B, wherein the post sections 522A-B extend through the first and second open slots 198A-B and the head portions 523A-B are coated on the opposite side of the housing wall 114. The upper portion 150 of the housing 102 is then positioned atop the lower portion 151 of the housing 102. The upper portion 150 comprises an upper section of the housing wall that also includes open slots that, when coupled to the lower portion 151, complete the housing wall 114 and form the first and second anchor apertures 116, 117.

Referring solely now to FIG. 25, the mouthpiece 101 is designed, in certain embodiments, such that the first light emitting surface 106 and the second light emitting surface 107 are located on opposite sides of a horizontal reference plane H-H. The first light emitting surface 106 is inclined so that a first acute angle θ1 is formed between with the first light emitting surface 106 and the horizontal reference plane H-H. The second light emitting surface 107 is inclined so that a second acute angle θ2 is formed between with the second light emitting surface 107 and the horizontal reference plane H-H.

The bite platform 105 extends from the first and second light emitting surfaces 106, 107 along the horizontal reference plane H-H. In one embodiment, the first and second acute angles θ1, θ2 are different from one another. In another embodiment, the first and second acute angles θ1, θ2 are the same. Each of the first and second acute angles θ1, θ2 are in a range of 75° to 89°.

As can be seen, the lower edge 306A of the first lamp 300A is horizontally offset from the upper edge 305B of the second lamp 300B. Moreover, the first and second lamps 200A-B are horizontally offset from one another such that the first lamp 300A is closer to the housing 102 than the second lamp 300B when measured along the reference plane H-H. In certain embodiments, the body of the mouthpiece 101 can be formed of a singular component that comprises a lamps support surface to which the first and/or second lamps are mounted.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral treatment device comprising:
 an intraoral mouthpiece comprising:
  a lamp support structure comprising a lamp support surface;
  first and second lamps, each of the first and second lamps comprising a plurality of light emitters that generate light which is emitted from a rear surface of the lamp;
  each of the first and second lamps mounted to the lamp support surface, thereby forming a lamp assembly, each of the first and second lamps operably coupled to a control circuit having a power source; and
  a lamp retaining component coupled to the lamp support structure, a lower portion of the first lamp and an upper portion of the second lamp retained between the lamp retaining component and the lamp support surface of the lamp support structure;
 wherein the first and second lamps are separated by a gap, a portion of the lamp retaining component extending through the gap and coupled to the lamp support structure.

2. The oral treatment device according to claim 1 further comprising:
 each of the first and second lamps comprising:
  a flexible sheet body having a front surface and a rear surface, the rear surface of the flexible sheet body forming the rear surface of the lamp; and
  the plurality of light emitters embedded within the flexible sheet body; and
 wherein each of the first and second lamps are mounted to the lamp support surface so that the rear surface of the flexible sheet body of each of the first and second lamps assumes a concave curvature; and
 wherein a lower portion of the flexible sheet body of the first lamp and an upper portion of the flexible sheet body of the second lamp is retained between the lamp retaining component and the lamp support surface of the lamp support structure.

3. The oral treatment device according to claim 2 wherein the lamp retaining component comprises a first arched surface that contacts the lower portion of the flexible sheet body of the first lamp and a second arched surface that contacts the upper portion of the flexible sheet body of the second lamp.

4. The oral treatment device according to claim 3 wherein the first and second arched surfaces of the lamp retaining component are horizontally offset from one another.

5. The oral treatment device according to claim 2 wherein, for each of the first and second lamps, the flexible sheet body comprises a flexible lens plate and a flexible reflective layer, the plurality of light emitters disposed between the flexible lens plate and the flexible reflective layer, and wherein a rear surface of the flexible lens plate forms the rear surface of the flexible sheet body.

6. The oral treatment device according to claim 5 wherein, for each of the first and second lamps, the flexible sheet body comprises first and second electrical contacts for supplying electrical energy from the power source to the plurality of light emitters, each of the first and second electrical contacts having a contact surface that forms a portion of the front surface of the flexible sheet body of the lamp.

7. The oral treatment device according to claim 5 wherein the plurality of light emitters are light emitting diodes printed to a front surface of the flexible lens plate.

8. The oral treatment device according to claim 2 wherein the intraoral mouthpiece further comprises:
   a guard component coupled to the lamp assembly, the guard component comprising:
      a first frame portion defining a first window through which the rear surface of the flexible sheet body of the first lamp is exposed;
      a second frame portion defining a second window through which the rear surface of the flexible sheet body of the second lamp is exposed; and
      a bite platform portion located between the first and second lamps, the lamp retaining component embedded in the bite platform portion.

9. The oral treatment device according to claim 8 wherein the lamp support structure comprises a plurality of depressions formed into the lamp support surface; and wherein the guard component comprises a pad portion filling each of the depressions.

10. The oral treatment device according to claim 8 wherein the guard component is an integrally formed monolith mass of an elastomeric material.

11. The oral treatment device according to claim 1 wherein the lamp retaining component snap-locks to the lamp support structure.

12. The oral treatment device according to claim 1 wherein the lamp retaining component comprises a plate portion extending horizontally from the lamp support surface.

13. The oral treatment device according to claim 1 further comprising:
   a housing containing the control circuit; and
   the intraoral mouthpiece coupled to and extending from the housing; and
   wherein the lamp support structure comprises an anchor element extending from a front surface of the lamp support structure that mates with the housing to fix the light assembly to the housing.

14. The oral treatment device according to claim 1 wherein the lamp support structure comprises a lamp registration feature that maintains the first and second lamps in selected positions relative to the lamp support structure.

15. The oral treatment device according to claim 1 wherein the lamp support structure comprises an upper curved edge, a lower curved edge, a first side edge extending between the upper and lower curved edges, and a second side edge extending between the upper and lower curved edges; and further comprising a guard component coupled to the lamp assembly, the guard component comprising a first wing portion extending beyond the first side edge of the lamp support structure and a second wing portion extending beyond the second side edge of the lamp support structure.

16. An oral treatment device comprising:
   an intraoral mouthpiece comprising:
      a lamp support structure comprising a lamp support surface;
      first and second lamps, each of the first and second lamps comprising a plurality of light emitters and a substrate, the plurality of light emitters mounted to the substrate and generating light which is emitted from a rear surface of the lamp;
      each of the first and second lamps mounted to the lamp support surface, thereby forming a lamp assembly, each of the first and second lamps operably coupled to a control circuit having a power source; and
      a lamp retaining component coupled to the lamp support structure, a lower portion of the first lamp and an upper portion of the second lamp retained between the lamp retaining component and the lamp support surface of the lamp support structure;
   wherein the substrates of the first and second lamps are distinct components.

* * * * *